US007985573B2

(12) United States Patent
Yacoby et al.

(10) Patent No.: US 7,985,573 B2
(45) Date of Patent: Jul. 26, 2011

(54) TARGETED DRUG-CARRYING BACTERIOPHAGES

(75) Inventors: Iftach Yacoby, Kfar Hess (IL); Eliora Z. Ron, Tel Aviv (IL); Doron Shabat, Tel Aviv (IL); Marina Shamis, Hadera (IL); Itai Benhar, Rehovot (IL)

(73) Assignee: Ramot At Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 11/850,942

(22) Filed: Sep. 6, 2007

(65) Prior Publication Data

US 2008/0057038 A1 Mar. 6, 2008

Related U.S. Application Data

(63) Continuation of application No. PCT/IL2006/000309, filed on Mar. 8, 2006.

(60) Provisional application No. 60/659,072, filed on Mar. 8, 2005.

(51) Int. Cl.
*C12N 7/00* (2006.01)
*A01N 63/00* (2006.01)
(52) U.S. Cl. .................................. 435/235.1; 424/93.2
(58) Field of Classification Search .................. None
See application file for complete search history.

(56) References Cited

U.S. PATENT DOCUMENTS

| | | | | |
|---|---|---|---|---|
| 5,427,908 | A | 6/1995 | Dower et al. | 435/5 |
| 5,580,717 | A | 12/1996 | Dower et al. | 435/5 |
| 5,698,424 | A | 12/1997 | Mastico et al. | 435/172.3 |
| 6,159,728 | A | 12/2000 | Stockley et al. | 435/320.1 |
| 6,387,397 | B1 | 5/2002 | Chen et al. | 424/450 |
| 6,448,083 | B1 | 9/2002 | Larocca et al. | 435/456 |
| 6,451,527 | B1 | 9/2002 | Larocca et al. | 435/6 |
| 6,485,902 | B2 | 11/2002 | Waddell et al. | 435/5 |
| 2002/0034733 | A1 | 3/2002 | Lohning | 435/5 |
| 2002/0044922 | A1 | 4/2002 | Mardh | 424/93.6 |
| 2003/0216338 | A1 | 11/2003 | Merril et al. | 514/44 |
| 2004/0011648 | A1 | 1/2004 | Paul et al. | 204/450 |
| 2004/0014652 | A1 | 1/2004 | Trouet et al. | 514/12 |
| 2004/0121974 | A1 | 6/2004 | March | 514/44 |
| 2004/0161431 | A1 | 8/2004 | Carlton et al. | 424/184.1 |
| 2005/0255462 | A1 | 11/2005 | Barrett et al. | 435/5 |

FOREIGN PATENT DOCUMENTS

| | | |
|---|---|---|
| WO | WO 91/17271 | 11/1991 |
| WO | WO 93/00434 | 1/1993 |
| WO | WO 98/05344 | 2/1998 |
| WO | WO 00/33888 | 6/2000 |
| WO | WO 00/53236 | 9/2000 |
| WO | WO 01/05950 A2 | 1/2001 |
| WO | WO 01/23619 A1 | 4/2001 |
| WO | WO 02/076498 A2 | 10/2002 |
| WO | WO 02/077182 A2 | 10/2002 |
| WO | WO 03/035611 A1 | 5/2003 |
| WO | WO 03/086276 A2 | 10/2003 |
| WO | WO 2004/052274 A2 | 6/2004 |
| WO | WO 2004/062677 A1 | 7/2004 |

OTHER PUBLICATIONS

Hart et al., Cell Binding and Internalization by Filamentous Phage Displaying a Cyclic Arg-Gly-Asp-containing Peptide, Journal of Biological Chemistry, 1994, 269(17):12468-12474.*
Larocca et al., Gene transfer to mammalian cells using genetically targeted filamentous bacteriophage, FASEB J. 13, 727-734 (1999).*
Bastien et al., "Protective Immune Responses Induced by the Immunization of Mice with a Recombinant Bacteriophage Displaying an Epitope of the Human Respiratory Syncytial Virus," Virology 234, 118-122 (1997).
Benhar et al., "Highly Efficient Selection of Phage Antibodies Mediated by Display of Antigen as Lpp-OmpA' Fusions on Live Bacteria," J. Mol. Biol. (2000) 301, 893-904.
Benhar et al., "Tumor Targeting by Antibody-Drug Conjugates," CRC Press, Inc., 1997, 73-85.
Brown et al., "RNA Bacteriophage Capsid-Mediated Drug Delivery and Epitope Presentation," Intervirology 2002; 45:371-380.
Clark et al., "Bacteriophage-mediated nucleic acid immunization," FEMS Immunology and Medical Microbiology 40 (2004) 21-26.
Delmastro et al., "Immunogenicity of filamentous phage displaying peptide mimotopes after oral administration," Vaccine, vol. 5, No. 11, pp. 1276-1285, 1997.
Felnerova et al., "Liposomes and virosomes as delivery systems for antigens, nucleic acids and drugs," Current Opinion in Biotechnology 2004, 15:518-529.
Garcea et al., "Virus-like particles as vaccines and vessels for the delivery of small molecules," Current Opinion in Biotechnology 2004, 15:513-517.
Haimovich et al., "Protein-Bacteriophage Conjugates: Application in Detection of Antibodies and Antigens," Science, vol. 164, pp. 1279-1280, Jun. 13, 1969.
Haus-Cohen et al., "Disruption of P-Glycoprotein Anticancer Drug Efflux Activity by a Small Recombinant Single-Chain Fv Antibody Fragment Targeted to an Extracellular Epitope," Int. J. Cancer: 109, 750-758 (2004).
Kassner et al., "Genetic Selection of Phage Engineered for Receptor-Mediated Gene Transfer to Mammalian Cells," Biochemical and Biophysical Research Communications 264, 921-928 (1999).

(Continued)

*Primary Examiner* — Zachariah Lucas
*Assistant Examiner* — Nicole Kinsey White
(74) *Attorney, Agent, or Firm* — Browdy and Neimark, PLLC

(57) ABSTRACT

The present invention relates to the field of drug delivery. More specifically, the invention relates to the preparation and use of a bacteriophage conjugated through a labile/non labile linker or directly to at least 1,000 therapeutic drug molecules such that the drug molecules are conjugated to the outer surface of the bacteriophage. The bacteriophage optionally displays on its coat a ligand that endows it with specificity towards target cells. Thus, there is provided a targeted, high-capacity drug delivery system useful for the treatment of various pathological conditions.

39 Claims, 11 Drawing Sheets

OTHER PUBLICATIONS

Larocca et al., "Receptor-mediated gene transfer by phage-display vectors: applications in functional genomics and gene therapy," DDT vol. 6, No. 15, 793-801, Aug. 2001.

Larocca et al., "Receptor-Targeted Gene Delivery Using Multivalent Phagemid Particles," Molecular Therapy vol. 3, No. 4, 476-484, Apr. 2001.

Mazor et al., "Humanization and epitope mapping of the H23 anti-MUC1 monoclonal antibody reveals a dual epitope sepecificity," Molecular Immunology 42 (2005) 55-69.

Menendez et al., "Immunisation with phage-displayed variable region 2 from meningococcal PorA outer membrane protein induces bactericidal antibodies against *Neisseria meningitides*," Immunology Letters 39 (2001) 143-148.

Meola et al., "Derivation of Vaccines From Mimotopes—Immunologic Properties of Human Hepatitis B Virus Surface Antigen Mimotopes Displayed on Filamentous Phage," The Journal of Immunology, 1995, 154: 3162-3172.

Merrill et al., "Long-circulating bacteriophage as antibacterial agents," Proc. Natl. Acad. Sci. USA, vol. 93, pp. 3188-3192, Apr. 1996.

Mikawa et al., "Surface Display of Proteins on Bacteriophage λ Heads," J. Mol. Biol. (1996) 262, 21-30.

Nakamura et al, "The effect of an agglutogen on virus infection: biotinylated filamentous phages and avidin as a model," Federation of European Biochemical Societies Letters 520 (2002) 77-80.

Nakamura et al., "A Visualization Method of Filamentous Phage Infection and Phage-Derived Proteins in *Escherichia coli* Using Biotinylated Phages," Biochemical and Biophysical Research Communications 289, 252-256 (2001).

Phalipon et al., "Induction of anti-carbohydrate antibodies by phage library-selected peptide mimics," Eur. J. Immunol. 1997, 27: 2620-2625.

Poul et al., "Selection of Tumor-Specific Internalizing Human Antibodies from Phage Libraries," J. Mol. Biol. (2000) 301, 1149-1161.

Poul et al., "Targeted Gene Delivery to Mammalian Cells by Filamentous Bacteriophage," J. Mol. Biol. (1999) 288, 203-211.

Sulica et al., "Detection of Antibody-Like Structures on Cell Surfaces with Chemically Modified Bacteriophages," The Journal of Immunology vol. 106, No. 3, Mar. 1971.

Summers, "Bacteriophage Therapy," Annu. Rev. Microbiol. 2001. 55:437-51.

Ulbrich et al., "Polymeric anticancer drugs with pH-controlled activation," Advanced Drug Delivery Reviews 56 (2004) 1023-1050.

Urbanelli et al., "Targeted Gene Transduction of Mammalian Cells Expressing the HER2/neu Receptor by Filamentous Phage," J. Mol. Biol. (2001) 313, 965-976.

White et al., "Antibody-Targeted Immunotherapy for Treatment of Malignancy," Annu. Rev. Med. 2001, 52:125-45.

Woiwode et al., "Synthetic Compound Libraries Displayed on the Surface of Encoded Bacteriophage," Chemistry & Biology, vol. 10, 847-858, Sep. 2003.

* cited by examiner

SEQUENCE LISTING

```
<160> NUMBER OF SEQ ID NOS: 13

<210> SEQ ID NO 1
<211> LENGTH: 525
<212> TYPE: PRT
<213> ORGANISM: Artificial Sequence
<220> FEATURE:
<223> OTHER INFORMATION: filamentous phage coat expressing the ZZ
      domain

<400> SEQUENCE: 1

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ser Ala Asn Leu Leu Ala Glu Ala Lys Lys Leu Asn Asp
            100                 105                 110

Ala Gln Ala Pro Lys Ala Ala Glu Thr Val Glu Ser Cys Leu Ala
        115                 120                 125

Lys Pro His Thr Glu Asn Ser Phe Thr Asn Val Trp Lys Asp Asp Lys
    130                 135                 140

Thr Leu Asp Arg Tyr Ala Asn Tyr Glu Gly Cys Leu Trp Asn Ala Thr
145                 150                 155                 160

Gly Val Val Val Cys Thr Gly Asp Glu Thr Gln Cys Tyr Gly Thr Trp
                165                 170                 175

Val Pro Ile Gly Leu Ala Ile Pro Glu Asn Glu Gly Gly Gly Ser Glu
```

```
                    180                 185                 190
Gly Gly Gly Ser Glu Gly Gly Ser Glu Gly Gly Thr Lys Pro
                195                 200                 205
Pro Glu Tyr Gly Asp Thr Pro Ile Pro Gly Tyr Thr Tyr Ile Asn Pro
            210                 215                 220
Leu Asp Gly Thr Tyr Pro Pro Gly Thr Glu Gln Asn Pro Ala Asn Pro
225                 230                 235                 240
Asn Pro Ser Leu Glu Glu Ser Gln Pro Leu Asn Thr Phe Met Phe Gln
                245                 250                 255
Asn Asn Arg Phe Arg Asn Arg Gln Gly Ala Leu Thr Val Tyr Thr Gly
            260                 265                 270
Thr Val Thr Gln Gly Thr Asp Pro Val Lys Thr Tyr Tyr Gln Tyr Thr
            275                 280                 285
Pro Val Ser Ser Lys Ala Met Tyr Asp Ala Tyr Trp Asn Gly Lys Phe
            290                 295                 300
Arg Asp Cys Ala Phe His Ser Gly Phe Asn Glu Asp Pro Phe Val Cys
305                 310                 315                 320
Glu Tyr Gln Gly Gln Ser Ser Asp Leu Pro Gln Pro Pro Val Asn Ala
                325                 330                 335
Gly Gly Gly Ser Gly Gly Gly Ser Gly Gly Ser Glu Gly Gly Gly
            340                 345                 350
Ser Glu Gly Gly Ser Glu Gly Gly Ser Glu Gly Gly Ser
            355                 360                 365
Gly Gly Gly Ser Gly Ser Gly Asp Phe Asp Tyr Glu Lys Met Ala Asn
            370                 375                 380
Ala Asn Lys Gly Ala Met Thr Glu Asn Ala Asp Glu Asn Ala Leu Gln
385                 390                 395                 400
Ser Asp Ala Lys Gly Lys Leu Asp Ser Val Ala Thr Asp Tyr Gly Ala
                405                 410                 415
Ala Ile Asp Gly Phe Ile Gly Asp Val Ser Gly Leu Ala Asn Gly Asn
            420                 425                 430
Gly Ala Thr Gly Asp Phe Ala Gly Ser Asn Ser Gln Met Ala Gln Val
            435                 440                 445
Gly Asp Gly Asp Asn Ser Pro Leu Met Asn Asn Phe Arg Gln Tyr Leu
450                 455                 460
Pro Ser Leu Pro Gln Ser Val Glu Cys Arg Pro Tyr Val Phe Gly Ala
465                 470                 475                 480
Gly Lys Pro Tyr Glu Phe Ser Ile Asp Cys Asp Lys Ile Asn Leu Phe
                485                 490                 495
Arg Gly Val Phe Ala Phe Leu Leu Tyr Val Ala Thr Phe Met Tyr Val
            500                 505                 510
Phe Ser Thr Phe Ala Asn Ile Leu Arg Asn Lys Glu Ser
            515                 520                 525

<210> SEQ ID NO 2
<211> LENGTH: 1578
<212> TYPE: DNA
<213> ORGANISM: Artificial Sequence
<220> FEATURE:
<223> OTHER INFORMATION: filamentous phage coat expressing the ZZ
      domain

<400> SEQUENCE: 2
atggtagaca caaattcaa caaagaacaa caaaacgcgt tctatgagat cttacattta      60
cctaacttaa acgaagaaca acgaaacgcc ttcatccaaa gtttaaaaga tgacccaagc    120
```

```
caaagcgcta accttttagc agaagctaaa aagctaaatg atgctcaggc gccgaaagta    180
gacaacaaat tcaacaaaga acaacaaaac gcgttctatg agatcttaca tttacctaac    240
ttaaacgaag aacaacgaaa cgccttcatc caaagtttaa agatgacccc aagccaaagc    300
gctaaccttt tagcagaagc taaaaagcta aatgatgctc aggcgccgaa agcggccgca    360
gaaactgttg aaagttgttt agcaaaacct catacagaaa attcatttac taacgtctgg    420
aaagacgaca aaactttaga tcgttacgct aactatgagg ctgtctgtg gaatgctaca    480
ggcgttgtgg tttgtactgg tgacgaaact cagtgttacg gtacatgggt tcctattggg    540
cttgctatcc ctgaaaatga gggtggtggc tctgagggtg gcggttctga gggtggcggt    600
tctgagggtg gcggtactaa acctcctgag tacggtgata cacctattcc gggctatact    660
tatatcaacc ctctcgacgg cacttatccg cctggtactg agcaaaaccc cgctaatcct    720
aatccttctc ttgaggagtc tcagcctctt aatactttca tgtttcagaa taataggttc    780
cgaaataggc agggtgcatt aactgtttat acgggcactg ttactcaagg cactgacccc    840
gttaaaactt attaccagta cactcctgta tcatcaaaag ccatgtatga cgcttactgg    900
aacggtaaat tcagagactg cgctttccat tctggcttta atgaggatcc attcgtttgt    960
gaatatcaag gccaatcgtc tgacctgcct caacctcctg tcaatgctgg cggcggctct   1020
ggtggtggtt ctggtggcgg ctctgagggt ggcggctctg agggtggcgg ttctgagggt   1080
ggcggctctg agggtggcgg ttccggtggc ggctccggtt ccggtgattt tgattatgaa   1140
aaaatggcaa acgctaataa gggggctatg accgaaaatg ccgatgaaaa cgcgctacag   1200
tctgacgcta aaggcaaact tgattctgtc gctactgatt acggtgctgc tatcgatggt   1260
ttcattggtg acgtttccgg ccttgctaat ggtaatggtg ctactggtga ttttgctggc   1320
tctaattccc aaatggctca agtcggtgac ggtgataatt cacctttaat gaataatttc   1380
cgtcaatatt taccttcttt gcctcagtcg gttgaatgtc gcccttatgt ctttggcgct   1440
ggtaaaccat atgaattttc tattgattgt gacaaaataa acttattccg tggtgtcttt   1500
gcgtttcttt tatatgttgc cacctttatg tatgtatttt cgacgtttgc taacatactg   1560
cgtaataagg agtcttaa                                                 1578
```

```
<210> SEQ ID NO 3
<211> LENGTH: 117
<212> TYPE: PRT
<213> ORGANISM: Artificial Sequence
<220> FEATURE:
<223> OTHER INFORMATION: ZZ domain

<400> SEQUENCE: 3
```

Met Val Asp Asn Lys Phe Asn Lys Glu Gln Gln Asn Ala Phe Tyr Glu
1               5                   10                  15

Ile Leu His Leu Pro Asn Leu Asn Glu Glu Gln Arg Asn Ala Phe Ile
            20                  25                  30

Gln Ser Leu Lys Asp Asp Pro Ser Gln Ser Ala Asn Leu Leu Ala Glu
        35                  40                  45

Ala Lys Lys Leu Asn Asp Ala Gln Ala Pro Lys Val Asp Asn Lys Phe
    50                  55                  60

Asn Lys Glu Gln Gln Asn Ala Phe Tyr Glu Ile Leu His Leu Pro Asn
65                  70                  75                  80

Leu Asn Glu Glu Gln Arg Asn Ala Phe Ile Gln Ser Leu Lys Asp Asp
                85                  90                  95

Pro Ser Gln Ser Ala Asn Leu Leu Ala Glu Ala Lys Lys Leu Asn Asp
            100                 105                 110

Ala Gln Ala Pro Lys
        115

<210> SEQ ID NO 4
<211> LENGTH: 351
<212> TYPE: DNA
<213> ORGANISM: Artificial Sequence
<220> FEATURE:
<223> OTHER INFORMATION: ZZ domain

<400> SEQUENCE: 4

```
atggtagaca acaaattcaa caaagaacaa caaaacgcgt tctatgagat cttacattta      60
cctaacttaa acgaagaaca acgaaacgcc ttcatccaaa gtttaaaaga tgacccaagc     120
caaagcgcta accttttagc agaagctaaa aagctaaatg atgctcaggc gccgaaagta     180
gacaacaaat tcaacaaaga acaacaaaac gcgttctatg agatcttaca tttacctaac     240
ttaaacgaag aacaacgaaa cgccttcatc caaagtttaa aagatgaccc aagccaaagc     300
gctaaccttt tagcagaagc taaaaagcta aatgatgctc aggcgccgaa a              351
```

<210> SEQ ID NO 5
<211> LENGTH: 13
<212> TYPE: PRT
<213> ORGANISM: Artificial Sequence
<220> FEATURE:
<223> OTHER INFORMATION: peptide

<400> SEQUENCE: 5

Gln Arg Gly Pro Asp Thr Arg Pro Val Ile Ala Ala Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: peptide

<400> SEQUENCE: 6

Ser Pro Gly His Tyr Trp Asp Thr Lys Leu Val Asp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: peptide

<400> SEQUENCE: 7

Thr Tyr Phe Pro Thr Met Gly Thr Ser Phe Lys Ile
1               5                   10

<210> SEQ ID NO 8
<211> LENGTH: 12
<212> TYPE: PRT
<213> ORGANISM: Artificial Sequence
<220> FEATURE:
<223> OTHER INFORMATION: peptide

<400> SEQUENCE: 8

Thr Phe Leu Arg Gly Pro Ser Ser Pro Leu Val Ser
1               5                   10

<210> SEQ ID NO 9

```
<211> LENGTH: 12
<212> TYPE: PRT
<213> ORGANISM: Artificial Sequence
<220> FEATURE:
<223> OTHER INFORMATION: peptide

<400> SEQUENCE: 9

Val His Met Val Ala Gly Pro Gly Arg Glu Pro Thr
1               5                   10

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
ccgcttccat ggtagacaac aaattcaaca aag                                   33

<210> SEQ ID NO 11
<211> LENGTH: 39
<212> TYPE: DNA
<213> ORGANISM: Artificial Sequence
<220> FEATURE:
<223> OTHER INFORMATION: primer

<400> SEQUENCE: 11
gggtttagcg gccgctttcg gcgcctgagc atcatttag                             39

<210> SEQ ID NO 12
<211> LENGTH: 36
<212> TYPE: DNA
<213> ORGANISM: Artificial Sequence
<220> FEATURE:
<223> OTHER INFORMATION: primer

<400> SEQUENCE: 12
aatttcggcc gacgtggcca tggcccaggt caaact                                36

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tattcacaaa cgaatggatc c                                                21
```

TARGETED DRUG-CARRYING BACTERIOPHAGES

CROSS-REFERENCE TO RELATED APPLICATIONS

This application is a continuation of International application PCT/IL2006/000309 filed Mar. 8, 2006, and claims the benefit of application 60/659,072 filed Mar. 8, 2005; the entire content of each of which is expressly incorporated herein by reference thereto.

FIELD OF THE INVENTION

The present invention provides bacteriophages conjugated through a linker or directly to a drug such that the drug is linked to the outer surface of the bacteriophage, the bacteriophage optionally displaying a targeting moiety, useful in targeted drug delivery.

BACKGROUND OF THE INVENTION

Targeted Therapy

Targeted drug delivery is a powerful technology which holds numerous potential advantages over conventional drug formulations. Methods for controlling the action of a drug in a specific temporal and spatial distribution, so as to direct its action to the desired target organ or cell, are currently being investigated to achieve increased safety and decreased side effects, increased bioavailability of the drug, improved dosage forms and administration schedules, and overall increased efficiency of the treatment. Since the development of methods of producing monoclonal antibodies (mAbs) by Köhler and Milstein, and the initial clinical trials of antibody therapy in cancer patients, there has been progress in antibody-based therapeutics, particularly in oncology. Early clinical trials with murine achieved biological effects principally by inducing immune effector functions (complement-dependent cytotoxicity, and antibody-dependent cellular cytotoxicity), which had the potential for therapeutic effect with minimal toxicity, as compared with standard chemotherapy. The range of possible therapeutic approaches with mAb targeted therapy was similarly impressive, with the possible selective delivery of isotopes, drugs, toxins and other cytotoxic materials to tumors by linking these agents to tumor targeting mAbs. Subsequent trials in a wide range of tumor systems with numerous constructs, however, demonstrated the limitations of murine antibodies regarding immunogenicity and the development of human anti-mouse antibody responses, (White et al., 2001) and demonstrated that the effective targeting and treatment of most solid tumors may not be achieved successfully with murine constructs.

Recent developments in the fields of protein engineering and particularly in antibody engineering techniques have led to the production of improved targeting moieties, such as humanized mAb constructs, recombinant antibody fragments such as single-chain antibodies (scFvs), short peptides, non-antibody ligand-binding proteins and even non proteinaceous molecules such as carbohydrates. Still, targeted therapy is mostly focused on cancer, with limited attention to immune system and autoimmune disorders.

Immunoconjugates are bifunctional molecules that consist of a "targeting" domain that localizes in tumors coupled to a therapeutic moiety (Benhar and Pastan, 1997). Immunoconjugates, in the broadest definition, may utilize mAb, mAb fragments, hormones, peptides or growth factors to selectively localize cytotoxic drugs, plant and bacterial toxins, enzymes, radionuclide, photosensitizers, or cytokines to antigens expressed on tumor cells or on cells of the tumor neovasculature (White et al., 2001).

Another approach for controlling drug delivery includes targeted drug activation, i.e. the use of prodrugs, wherein the drug composition is inactive when administered, but is converted to active form in vivo through exposure to a particular physiologic environment or metabolic process. In some cases, the drug is linked to a masking moiety rendering it inactive, by means of a linker that can be, for example, acid-labile or enzyme-cleavable (Ulbrich and Subr, 2004). Examples for the use of this approach are WO 00/33888 and US 2004/014652.

Other approaches for controlling drug delivery include the use of carriers, such as liposomes, microspheres and dendrimers, to alter the physico-chemical qualities of a drug, thus controlling its distribution and half-life.

These and other studies possess several advantages over the use of traditional drug formulations, but each methodology is limited by its own shortcomings, aside from technical challenges related to tissue penetration, stability and immunogenicity. For example, the extent to which drug disposition can be controlled through nonselective mechanisms, such as carriers and prodrugs, is limited. In addition, the drug carrying capacity of existing targeted therapies is a key issue in their potency, as some of the putative targeted molecules are only expressed in a limited copy number on the target cell.

Thus, attempts at providing targeted drug delivery methods combining the benefits of the different approaches are being made. For example, conjugation schemes, such as the use of dendrimers and branched linkers were devised to maximize the drug payload per targeting molecule that binds a target site. Other approaches include directed micelles, liposomes or polymers (see, for example, WO 03/035611, WO 00/53236, US 2004/11648 and U.S. Pat. No. 6,387,397), some of them utilizing viral components for target recognition and/or structural purposes (Felnerova et al., 2004, Garcea et al., 2004). However, despite the recent advances made in the field of targeted drug delivery, the need remains for developing new effective target-specific drug delivery methods.

Drug Resistant Bacteria

The increasing development of bacterial resistance to traditional antibiotics has reached alarming levels, thus necessitating the strong need to develop new antimicrobial agents. The use of antimicrobial drugs for prophylactic or therapeutic purposes in humans, or for veterinary or agricultural purposes, has provided the selective pressure favoring the survival and spread of resistant organisms. Because of more intensive antibiotic use in hospitals as compared with the community, higher rates of resistance are noted in hospital pathogens, especially in the intensive care unit where infections caused by Gram-positive bacteria are increasing.

Attempts at discovering totally new agents effective in the treatment of bacterial disease caused by resistant organisms are currently being made. The large majority of marketed antibacterials have been targeted against the bacterial cell wall or macromolecular biosynthesis (DNA, RNA or protein). Bacteria have, however, developed defenses, either by mutation or by acquiring new genes from other bacteria.

These defenses have included acquiring enzymes to deactivate the drugs, alteration in permeability of cell walls, efflux proteins to pump antibacterial rapidly out of cells and alteration of target molecules in order to protect them against attack by antibacterials. However, for the first time in several years, new classes of compounds designed to avoid defined resistance mechanisms are undergoing clinical evaluation. Classical short-term approaches include chemical modification of existing agents to improve potency or spectrum. Long-term approaches are relying on bacterial and phage genomics to discover new antibiotics that attack new protein targets which are essential to bacterial survival and therefore with no known resistance. The rationale of such approaches is that the only certain way to avoid encountering previously generated resistance is to seek new antibiotic targets.

In both traditional and newly developed antibiotics, the target selectivity lies in the drug itself, in its ability to affect a mechanism that is unique to the target microorganism and absent in its host. As a result, a vast number of potent drugs have been excluded from use as therapeutics due to low selectivity, i.e. toxicity to the host as well as to the pathogen.

Therapeutic Use of Bacteriophages

Bacteriophages (phages) are a phylum of viruses that infect bacteria, and are distinct from plant or animal viruses. Upon infection of a corresponding host bacterium, the phages may undergo a "lytic" life cycle, a "lysogenic" life cycle that can potentially become lytic, or a "non-lytic" life cycle. Virulent Phages replicate through the lytic cycle, causing lysis of the host bacterial cell as a normal part of their life cycles. Temperate phages can undergo either a "lysogenic" life cycle, in which the phage may be integrated into the bacterial host DNA to persist as a prophage, or replicate by means of the lytic life cycle and cause lysis of the host bacterium. The natural capability of phages to selectively infect a host bacterium and to kill it is the basic concept upon which "phage therapy" was built. Phage therapy was pioneered by D'herelle, who recognized bacteriophages as epizootic infections of bacteria Phages were almost immediately deployed for antibacterial therapy and prophylaxis by D'herelle, and later on by others. Although many early phage therapy trials were reported successful, and many of the major pharmaceutical firms sold phage preparations (e.g., Parke-Davis and Lilly in the United States), there were also failures. The early trials of bacteriophage therapy for infectious diseases were thus confounded, because the biological nature of bacteriophage was poorly understood. Therefore, the advent of antibiotics resulted in the absence of rigorous evaluations of phage therapy until very recently. However, recent laboratory and animal studies, exploiting current understandings of phage biology, suggest that phages may be useful as antibacterial agents in certain conditions (reviewed in Summers, 2001).

The therapeutic application of phages as antibacterial agents is still impeded by several factors: (i) the failure to recognize the relatively narrow host range of phages; (ii) the presence of toxins in crude phage lysates; and (iii) a lack of appreciation for the capacity of mammalian host defense systems, particularly the organs of the reticuloendothelial system, to remove phage particles from the circulatory system (Merril et al., 1996). Solutions to the latter problem were proposed in the form of selecting long-circulating phage mutants that escape or even repel the host defense system (Merril et al., 1996) or modifying the phage coat with i.e. polyethylene glycol to "shield it" from host defense surveillance mechanisms (US patent application 2004/0161431).

To date, most attempts at anti bacterial phage therapy still rely on the exquisite specificity of phages to infect (and kill) a unique host bacterium (for example U.S. Pat. No. 6,485, 902, PCT application WO 2004/052274 and references therein), although a few attempts at creating bacteriophages with a broader host spectrum as an anti-bacterial therapy have been reported (US 2002/0044922 and US 2003/216338).

WO 2004/062677 discloses compositions for treating a bacterial biofilm, comprising a first bacteriophage that is capable of infecting a bacterium within said biofilm, and a first polysaccharide lyase enzyme that is capable of degrading a polysaccharide within said biofilm. The composition preferably further comprises a pharmaceutically-acceptable antimicrobial agent, and may also include a DNase.

The growing use of bacteriophages as molecular biology tools has led to the development of another therapeutic use for phages, namely phage-mediated gene delivery to mammalian cells. This technology was developed following discoveries by several groups that identified "internalizing phages" while searching for cell-surface molecules that could be used as targets in targeted immunotherapy. Antibodies that bind cell surface receptors in a manner whereby they are endocytosed are useful molecules for the delivery of drugs, toxins, or DNA into the cytosol of mammalian cells for therapeutic applications. Traditionally, internalizing antibodies have been identified by screening hybridomas. Several groups turned to phage display as an alternative approach. In a pioneering work from the Marks group, an anti ErbB2 antibody was used to determine the feasibility of directly selecting internalizing antibodies from phage libraries and to identify the most efficient display format. Using a known antibody in a scFv format, displayed monovalently on a phagemid, they demonstrated that anti-ErbB2 phage antibodies can undergo receptor-mediated endocytosis. This study also defined the role of affinity, valency, and display format on the efficiency of phage endocytosis and identified the factors that led to the greatest enrichment for internalization. This work demonstrated that phages displaying bivalent scFvs (diabodies) or multiple copies of the scFv were more efficiently endocytosed than phage displaying monomeric scFv (Becerril et al., 1999).

Subsequent studies have further demonstrated the use of internalizing phages as gene delivery vessels. Vectors based on filamentous phages, lambdoid phages or phagemids, carrying antibodies or ligands of mammalian internalizing cell surface receptors, have been reported (see, for example, Kassner et al., 1999, Poul and Marks, 1999, Larocca and Baird, 2001, Larocca et al., 2001, Urbanelli et al., 2001, U.S. Pat. Nos. 6,451,527, 6,448,083, and International Application WO 98/05344).

Additional phage-based therapeutic approaches use whole phage particles for vaccination. Initially, phage lysates were used as immunogens with the aim of eliciting immune response against components of the phage bacterial host that are present in the lysate. Following the utilization of phage display for the identification of antibody epitopes and mimotopes, several groups used the peptide-displaying phages as immunogens to elicit an immune response against the original pathogen or diseased tissue from which the epitope originated, which met with limited success (Meola et al., 1995; Bastien et al., 1997; Delmastro et al., 1997; Phalipon et al., 1997; Menendez et al., 2001). With the advent of DNA vaccination, phages were adapted as carriers of DNA for similar purposes. This fledgling field was developed as an outgrowth of phage-mediated gene delivery approaches following the identification of cell-internalizing phages (Becerril et al., 1999; Poul and Marks, 1999; Poul et al., 2000). Recent studies have shown that bacteriophage-mediated DNA vaccination consistently gave better antibody responses when compared to naked DNA. Although a strong antibody response was also seen against the carrier phage coat proteins, this may actually enhance the efficiency of the delivery system, since the formation of immune complexes should more effectively target APCs following boosting (Clark and March, 2004, WO 02/076498, US 2004/0121974).

Several reports disclose bacteriophages linked to haptens for experimental purposes. For example, Haimovich and colleagues (Haimovich and Sela, 1969; Sulica et al., 1971) report the generation of protein-bacteriophage conjugates useful in detection of antibodies and antigens. These studies did not teach or disclose pharmaceutical compositions comprising protein-bacteriophage conjugates.

Other studies disclose particles of bacteriophage components that contain or enclose drugs for therapeutic uses. Brown et al. (2002) discloses a virus-like particle comprising recombinant MS2 coat proteins and a toxin molecule conjugated to an RNA molecule. U.S. Pat. No. 6,159,728 discloses a delivery system comprising a capsid formed from a coat protein of a bacteriophage selected from the group consisting of MS-2, R17, fr, GA, Qβ, and SP and a foreign moiety enclosed in the capsid, wherein the foreign moiety is of a size sufficiently small to be enclosed in the capsid and wherein the foreign moiety is linked to a RNA sequence comprising a translational operator of the bacteriophage, which translational operator binds to the coat protein during formation of the capsid.

However, none of the background art discloses pharmaceutical compositions having high drug-binding ratios on bacteriophage-based drug carriers suitable for targeted drug delivery. The development of an efficient, high-capacity system for drug delivery would be highly advantageous in the treatment of various diseases, such as cancer, bacterial and viral infections and any disease expressing specific and targetable markers.

SUMMARY OF THE INVENTION

The present invention provides bacteriophage-drug conjugates having improved drug loading capacity. The present invention further provides bacteriophage-drug conjugates that comprise an exogenous targetor. The exogenous targetor can be advantageously expressed in genetically modified bacteriophages, or can be linked to an anchor on the bacteriophage. The present invention further provides pharmaceutical compositions comprising a bacteriophage useful in targeted drug delivery, the bacteriophage conjugated to a drug, either directly or via a linker, and optionally displays a targeting moiety.

The invention provides a novel and unexpectedly effective means of delivering drugs specifically to target cells. The invention demonstrates for the first time the efficacy of targeted bacteriophage-drug conjugates wherein the therapeutic drug is linked to the outer surface of the bacteriophage. The drug-carrying capacity of the novel bacteriophage carriers of the invention is thus significantly higher than that of hitherto known viral-based vectors, as it is not limited by the size of the capsid vessel. Advantageously, according to some currently preferred embodiments of the invention the bacteriophages may be filamentous phages that offer a large number of sites for binding the drug molecules. For example, about $10^3$ drug molecules or more may be delivered by a single filamentous phage to each target site at the target cell. As a result, even drugs that lack organism selectivity and have been thus far excluded from use, or drugs with narrow therapeutic windows as are most current anti-cancer drugs, could be used while harm to the treated individual is minimized.

In contradistinction to previously reported viral-based vessels, efficient drug delivery according to the invention does not necessitate the internalization of the bacteriophage carrier. Therefore, the target-cell binding entities displayed on the surface of the bacteriophage may be directed to a cellular target selected from a broad array of possible targets.

According to a first aspect, the invention provides a bacteriophage conjugated to a drug or isotope, wherein the drug or isotope is linked to the outer surface of the bacteriophage. In one embodiment, the bacteriophage-drug conjugates of the invention comprise an average of at least about 1,000, preferably at least about 3,000, more preferably at least about 5,000, and most preferably at least about 10,000 drug molecules linked to each bacteriophage. In one embodiment, the drug molecules are covalently linked to said bacteriophage.

In one embodiment, the bacteriophage is a filamentous phage. In a preferred embodiment, the filamentous phage is selected from a group consisting of *Escherichia coli* infecting phages m13, Fd, and f1. In another embodiment, the bacteriophage is a lambdoid phage. In another embodiment, the phage particle carries a genetically modified phage genome vector. In another embodiment, the phage particle carries a genetically modified hybrid vector (phagemid).

In one embodiment, the drug is a compound that upon its accumulation in the target cell results in the killing of said target cell or retardation of its growth or replication.

In another embodiment, the drug is selected from a group consisting of: an antibacterial agent, an antibiotic, an anti fungal drug, an anti viral drug, a parasiticide, a compound that kills mammalian cells or inhibits their growth, and isotopes (including, but not limited to: halogens, metals and radioactive isotopes). In other embodiments, the drug is a compound useful for the treatment of a disease or disorder e.g. metabolic, psychiatric, hormonal or organ specific compounds. In yet another embodiment, the bacteriophage is linked to a combination of multiple drugs.

The drug may be conjugated to the bacteriophage by a stable or labile linker. In the latter case, the drug may effectively be kept in an inactive prodrug state that is released as an active drug at the target. Optionally, branched linkers or dendrimers facilitate high-load conjugation of hydrophobic drugs and enable simultaneous delivery of multiple compounds to the target cell, allowing drug synergy. The solubility as well as the pharmacokinetic and pharmacodynamic behavior of a conjugated drug differ significantly from those of the corresponding free drug, enabling the use of poorly soluble drugs for human and livestock therapy. The invention may further possess additional advantages, as it allows utilization of the natural anti-bacterial abilities of bacteriophages, as well as their ability to mediate targeted gene delivery.

In another embodiment, the bacteriophage is conjugated to the drug via a linker. In one embodiment, the linker is a stable linker. In another embodiment, the linker is a labile linker, allowing controlled release of the drug at the target site. In another embodiment, the drug is conjugated to the bacteriophage in an inactive prodrug form, and released as an active drug upon the cleavage of the linker at the target site. According to various embodiments, the labile linker may be enzyme-cleavable, acid-labile, or comprise a disulfide bond. In one embodiment, the release of the drug is facilitated by an enzymatic activity present on the surface of the target cell. In another embodiment, the release of the drug is facilitated by an enzymatic activity present inside the target cell. In yet another embodiment, the release of the drug is facilitated by an enzymatic activity present in bodily fluids such as serum. In a further embodiment, the release of the drug is facilitated by the administration of an exogenous enzyme. In a different embodiment, the release of the drug is facilitated by acidic pH. In another embodiment, the release of the drug is facilitated by an enzyme encoded by a nucleic acid delivered to the target cell by the bacteriophage. In various embodiments, the release of the drug is facilitated by at least one enzyme selected from the group consisting of: proteases, peptidases, esterases, amidases, glycosidases and lipases. In one particular embodiment, the release of the drug is facilitated by an esterase (e.g. a serum esterase).

In another embodiment, the linker is selected from the group consisting of branched linkers and dendrimers. In one particular embodiment, the linker is an aminoglycoside (e.g. hygromycin and kanamycin).

In another embodiment, the bacteriophage-drug conjugate of the invention displays an exogenous targeting moiety that selectively binds a target molecule on a target cell.

In one embodiment, the bacteriophage is genetically modified to selectively bind a target cell. In one embodiment, the genetic modification results in the display of a ligand on the phage coat. In a preferred embodiment, the genetic modification is in the form of a targeting moiety-coding DNA sequence fused to a gene coding for a coat protein of the phage. In a preferred embodiment, the ligand is displayed by its fusion to the major coat protein (protein VII) of a filamentous phage. In another preferred embodiment, the ligand is displayed by its fusion to the minor coat protein (protein D) of a filamentous phage.

In another embodiment, the targeting moiety is linked to the phage by means of chemical conjugation.

In one embodiment, the ligand is a peptide endowed with binding specificity towards the target cell. In another embodiment, the ligand is a short peptide selected from a library of short peptide sequences that is endowed with binding specificity towards the target cell. In another embodiment, the ligand is an antibody or an antibody fragment that is endowed with binding specificity towards the target cell.

In another embodiment, the ligand is the ZZ domain derived from *Staphylococcus aureus* protein A that binds an antibody that is endowed with binding specificity towards the target cell, or an analog or derivative thereof. In one particular embodiment, the ZZ domain is fused to the coat protein of a filamentous bacteriophage. In another particular embodiments, coat protein is the minor coat protein of the bacteriophage. In another particular embodiment, there is provided a bacteriophage comprising a coat protein having an amino acid sequence as set forth in SEQ ID NO:1 and analogs thereof. In another particular embodiment, the coat protein is encoded by a nucleotide sequence having nucleic acid sequence as set forth in SEQ ID NO:2 and homologs thereof.

In another embodiment, the ligand is avidin or streptavidin that binds a biotinylated ligand that is endowed with binding specificity towards the target cell. In other embodiments, the ligand is a polypeptide, a carbohydrate, a lipid, a glycolipid, a saccharide, a nucleic acid and the like, which is able to selectively bind a target molecule on a target cell.

In yet another aspect, the ligand displayed by the targeted bacteriophage-drug conjugate of the invention is selected such that the conjugate is able to selectively bind a target cell involved in a disease or disorder in a subject in need thereof. In one embodiment, the target cell is a bacterial cell. In another embodiment, the target cell is a fungal cell. In another embodiment, the target cell is a yeast cell. In another embodiment, the target cell is a unicellular parasite (e.g. protozoa) cell. In another embodiment, the target cell is a multicellular parasite (e.g. helminth) cell. In another embodiment, the target cell is a virus-infected mammalian cell. In another embodiment, the target cell is a mammalian cell infected by a microorganism. In another embodiment, the target cell is a mammalian cell infected by a parasite. In another embodiment, the target cell is a tumor cell (for example, tumor cells wherein the target molecule to which the targeting moiety is directed is a tumor associated antigen such as MUC-1 and Tac). In another embodiment, the target cell is a cell that supports tumor growth such as tumor neovasculature. In another embodiment, the target cell is a diseased cell such as an outgrowth of muscle cells at a restenotic plaque, an epithelial cell in psoriasis, an immune cell involved in the development of an autoimmune disease, and any diseased or malfunctioning cell that may be targeted through a distinct surface molecule. In some cases, the cells to be treated may be selected based on cosmetic rather than strictly medical criteria, e.g. destruction of adipocytes to treat obesity.

In one embodiment, the subject in need thereof is a human subject. In another embodiment, the subject in need thereof is a mammal. In another embodiment, the subject in need thereof is a non-mammalian animal.

In another aspect, the invention provides pharmaceutical compositions comprising the bacteriophage-drug conjugates of the invention and optionally at least one pharmaceutically acceptable carrier, excipient or diluent.

In another aspect, the invention provides a method of treating a disease or disorder in a subject in need thereof, comprising administering to the subject a therapeutically effective amount of a pharmaceutical composition comprising a bacteriophage-drug conjugate of the invention.

In one embodiment, the disease or disorder includes, but is not limited to: hyperproliferative disorders; tumors; autoimmune diseases; restenosis; angiogenesis-dependent diseases; and infectious diseases caused by bacteria, viruses, yeast, fungi, and parasites.

In another aspect, the invention provides a method of treating a bacterial infestation, comprising exposing the bacteria to a pharmaceutical composition comprising a bacteriophage-drug conjugate. In one embodiment, the bacteriophage is capable of lysing said bacteria.

In yet another aspect, the invention provides a method of treating a disease or disorder in a subject in need thereof, comprising administering to the subject a therapeutically acceptable amount of a pharmaceutical composition comprising a bacteriophage-drug conjugate of the invention, wherein the bacteriophage comprises a nucleic acid molecule comprising an exogenous nucleic acid sequence that is expressible in the target cell.

In one embodiment, the exogenous nucleic acid sequence encodes an enzyme that is capable of cleaving the linker connecting the drug to the bacteriophage, thereby releasing the drug. In another embodiment, the exogenous gene encodes an antimicrobial peptide, an antibiotic, a toxin, an enzyme or a cytotoxic agent.

In another aspect, the invention is directed to the use of a pharmaceutical composition of the invention for the preparation of a medicament.

In another aspect, the invention is directed to the use of a bacteriophage-drug conjugate of the invention for the preparation of a pharmaceutical composition useful for the treatment of a disease or disorder selected from the group consisting of: hyperproliferative disorders; tumors; autoimmune diseases; restenosis; angiogenesis-dependent diseases; and infectious diseases caused by bacteria, viruses, yeast, fungi, and parasites.

In another aspect, the present invention provides a kit for generating a targeted bacteriophage-drug conjugate, comprising: (i) a bacteriophage-drug conjugate displaying a ligand capable of binding a targeting moiety that selectively binds a target molecule on a target cell; and (ii) instructions for linking the targeting moiety to the ligand. In certain particular embodiments, the ligand is selected from: the ZZ domain derived from *Staphylococcus aureus* protein A, avidin, streptavidin, biotin and analogs and derivatives thereof.

These and other embodiments of the present invention will become apparent in conjunction with the figures, description and claims that follow.

DETAILED DESCRIPTION OF THE INVENTION

Figure 1:
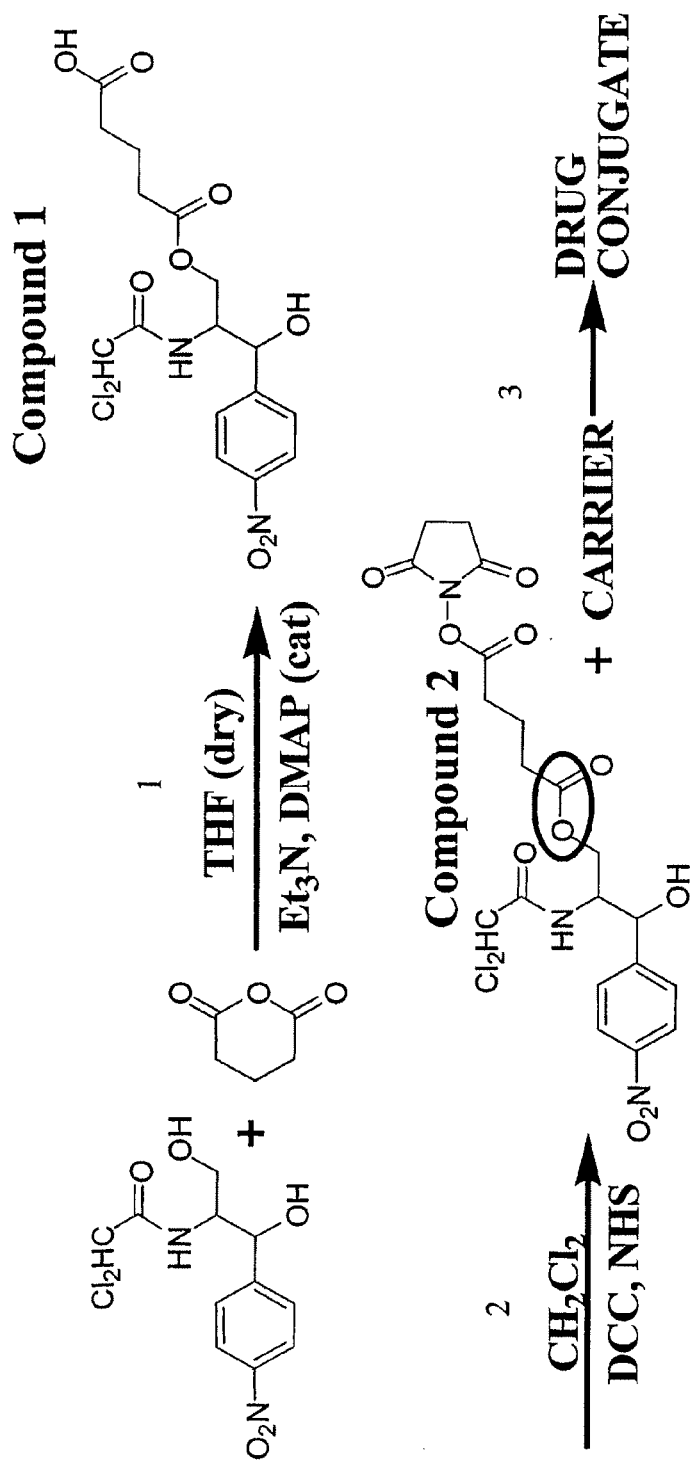
FIG. 1. Synthesis of CAM-liker adduct for conjugation to lysine groups. (A) Two chemical steps were used to modify chloramphenicol: In the first step (1), the chloramphenicol primary OH group was reacted with glutaric anhydride to create an ester linkage. In the second step (2), the free carboxyl group was activated with NHS to allow subsequent linkage to amine groups such as on lysines. At this stage the chloramphenicol-prodrug is not toxic and is ready for conjugation to proteins (3). The labile ester bond is marked by a circle.

The present invention relates to the field of drug delivery. More specifically, the invention relates to the preparation and use of genetically modified bacteriophages that display a ligand on their coat endowing them with specificity towards target cells. These bacteriophages are conjugated through a labile/non labile linker or directly to at least 1,000 drug molecules, such that the drug molecules are linked to the outer surface of each bacteriophage, and are thus useful as targeted drug delivery vessels for the treatment of various pathological conditions.

Bacteriophages

The terms "bacteriophage" and "phage" are used interchangeably herein to indicate a bacterial virus which forms a package consisting of a protein coat containing nucleic acid required for its replication. The nucleic acid may be DNA or RNA, either double or single stranded, linear or circular. Unless otherwise noted, the terms "bacteriophage" and "phage" also encompass "phagemid", i.e., a bacteriophage the genome of which includes a plasmid that can be excised and packaged by co-infection of a host with a helper phage.

According to a first aspect, the invention provides a bacteriophage conjugated to a drug. In one embodiment, said bacteriophage is covalently linked to the drug. In another embodiment, the bacteriophage is a filamentous phage. In a preferred embodiment, the filamentous phage is an *Escherichia coli* (*E. coli*) male-specific filamentous phage including, but not limited to: m13, Fd, and f1. In another embodiment, the bacteriophage is a lambdoid phage. In another embodiment, the phage particle carries a genetically modified phage genome vector. In another embodiment, the phage particle carries a genetically modified hybrid vector (phagemid). A large array of phage, phagemid and helper vectors are known to those of skill in the art (see, for example, Kay et al., 1996; Berdichevsky et al., 1999; Benhar, 2001).

The bacteriophage-drug conjugates of the invention comprise at least about 1,000, preferably at least about 3,000, more preferably at least about 5,000, and most preferably at least about 10,000 drug molecules conjugated to a bacteriophage. It should be explicitly understood that these numbers represent an average number of drug molecules per phage in the entire bacteriophage population. For example, a filamentous phage, as exemplified herein by m13 and fd, carries about 3,000 copies of its major coat protein p8, each containing about eight amine-containing residues that may be available for chemical conjugation. The present invention demonstrates the production of bacteriophage-drug conjugates having a drug carrying capacity at least about tenfold higher than hitherto known targeted drug delivery vessels. Similarly, any bacteriophage or virus expressing multiple copies of coat proteins on its surface, either naturally or by means of genetic modification, may be utilized for the production of conjugates according to the invention, so long as the drug carrying capacity of the conjugates of the invention is retained.

According to certain embodiments, the phage genome is genetically modified to display a targeting ligand, as will be described hereinbelow. In other embodiments, the genetic modification may serve properties unrelated to targeting. In a preferred embodiment said modification will serve to increase the viral genome size thereby increasing the virus size and the resulting number of conjugation sites per phage (the length of filamentous phage is dependent on the size of the packaged genome). In another preferred embodiment said modification will serve to enable the phage to delay inactivation by any and all of the host defense systems (see, e.g. U.S. Pat. No. 5,766,892). In other embodiments, the genetic modification allows the delivery and expression of genes in the target cell, as described hereinbelow. Methods for creating genetically modified phages are well known in the art (see, e.g., Sambrook et al., 1989).

For the construction of targeted bacteriophage-drug conjugates, phages may be propagated and maintained by methods well known in the art (Sambrook et al., 1989, Kay et al., 1996 and the Examples herein). For commercial scale production of these conjugates, large-scale bacteriophage production methods may be used (see, for example, WO 2004/052274).

Drugs

As used herein, the term "drug" refers to chemical and biological compounds, mixtures and materials, derivable from natural or artificial sources, which exert a therapeutic effect on a target disorder or condition. The active substance can be soluble or insoluble in water. The term "therapeutic effect" refers to an effect which reverses, arrests, slows the progression of, ameliorates or relieves symptoms of a target disorder or condition.

Figure 14:
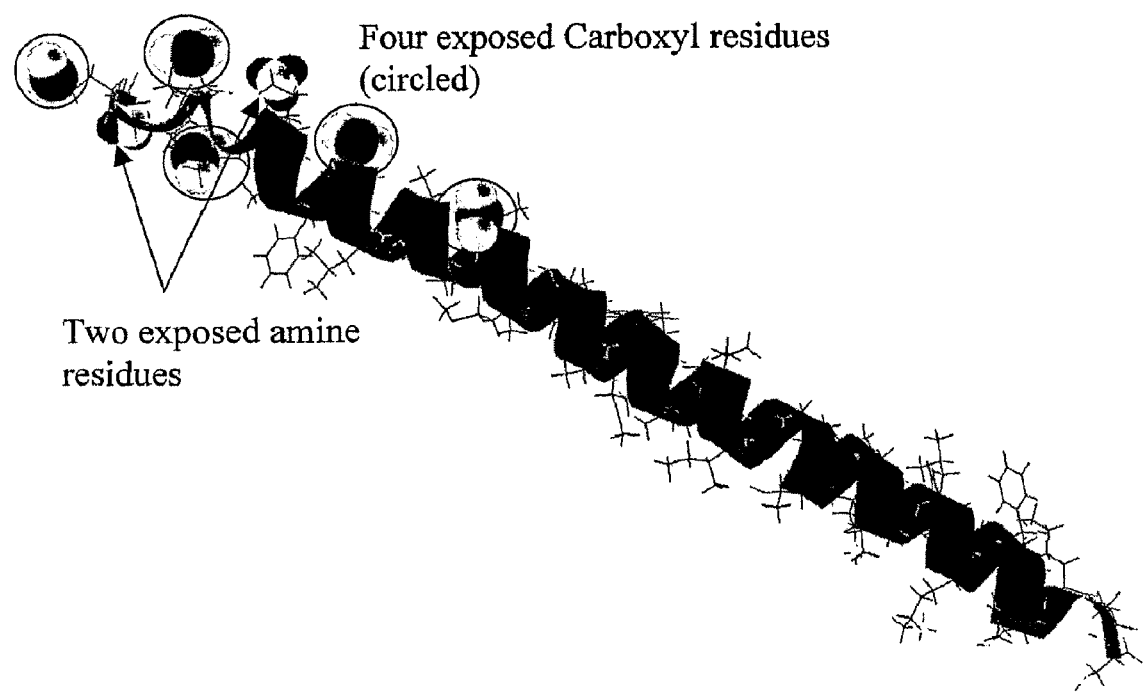
FIG. 14. Model of the phage P8 coat protein monomer. A structural model of a monomer of filamentous phage p8 major coat protein is shown with the positions of amine containing side chains (marked by arrows) and carboxyl containing side chains (circled) that are available to chemical modification highlighted. The coat of each phage particle is composed of some 3000 copies of P8. Based on PDB file 2COX.

The drug molecules constituting the conjugates of the invention are linked to the outer surface of the bacteriophage. In other words, the drug is exposed to the external environment and not enclosed inside a viral capsid or a virus-like particle. In certain embodiments, the drug is covalently linked to the outer surface of a coat protein of a bacteriophage. By means of a non-limitative example, FIG. 14 illustrates particular side chains of the fd p8 protein that are available for conjugating a drug via chemical modification: amine residues at N-terminus (alpha amine) and Lys 8 and carboxyl residues at Glu 2, Asp 4, Asp 5 and Asp 12.

According to certain embodiments, a bacteriophage-drug conjugate is administered to a subject in need thereof. In one embodiment, the drug is a compound that upon its accumulation in the target cell results in the killing of said target cell or inhibition of its growth or proliferation. In another embodiment, the drug is selected from a group consisting of: an antibacterial agent, an antibiotic, an anti fungal drug, an anti viral drug, a parasiticide, a compound that kills mammalian cells or inhibits their growth. In another embodiment, the bacteriophage is conjugated to an isotope including, but not limited to: halogens, metals and radioactive isotopes. In yet another embodiment, the bacteriophage is linked to a combination of multiple drugs.

Other non-limitative examples of drugs that can be used are psychotherapeutic and psychotropic drugs, ion channel blockers, hormones (e.g. insulin) enzymes (e.g. thrombin, collagenase and components of the complement system) and any metaboloic or organ specific agent (e.g. statin).

For certain applications, the drug is a cytotoxic or pharmacological agent, particularly cytotoxic agent (able to kill the target cell) or a cytostatic agent (having the ability to suppress the growth or cell division of the target cell). Exemplary anti-cellular agents include chemotherapeutic agents, as well as cytotoxins. Chemotherapeutic agents that may be used include: hormones, such as steroids; anti-metabolites, such as cytosine arabinoside; adriamycin, 5-fluorouracil (5FU), etoposide (VP-16), camptothecin, actinomycin-D, mitomycin C, cisplatin (CDDP), doxorubicin, etoposide, verapamil, podophyllotoxin, carboplatin, procarbazine, mechlorethamine, cyclophosphamide, ifosfamide, melphalan, chlorambucil, bisulfan, nitrosurea, dactinomycin, daunorubicin, bleomycin, plicomycin, mitomycin, tamoxifen, taxol, transplatinum, vincristin, vinblastin and methotrexate. Additional antineoplastic agents include those disclosed in Chapter 52, "Antineoplastic Agents" (Calabresi, P. and Chabner, B. A.), and the introduction thereto, pp. 1202-1263, of Goodman and Gilman, The Pharmacological Basis of Therapeutics, Eighth Edition, 1990, McGraw-Hill, Inc. (Health Professions Division). Other embodiments may include agents such as cytokines. In another embodiment the drug is a toxin including, but not limited to bacterial toxins (e.g. diphtheria toxin), plant toxins (e.g. ricin from jack bean), toxins of eukaryotic origin and other naturally occurring and man-made toxins.

In another embodiment the drug is an antimicrobial agent including, but not limited to: chloramphenicol (CAM), penicillin and drugs of the penicillin family of antimicrobial drugs, including but not limited to penicillin-G, penicillin-V, phenethicillin, ampicillin, amoxacillin, cyclacillin, bacampicillin, hetacillin, cloxacillin, dicloxacillin, methicillin, nafcillin, oxacillin, aziocillin, carbenicillin, mezlocillin, piperacillin, ticaricillin, and imipenim; cephalosporin and drugs of the cephalosporin family, including but not limited to cefadroxil, cefazolin, caphalexn, cephalothin, cephapirin, cephradine, cefaclor, cefamandole, cefonicid, cefoxin, cefuroxime, ceforanide, cefotetan, cefinetazole, cefoperazone, cefotaxime, ceftizoxime, ceftizone, moxalactam, ceftazidime, and cefixime; aminoglycoside drugs and drugs of the aminoglycoside family, including but not limited to streptomycin, neomycin, kanamycin, gentamycin, tobramycin, amikacin, and netilmicin; macrolide and drugs of the macrolide family, exemplified by azithromycin, clarithromycin, roxithromycin, erythromycin, lincomycin, and clindamycin; tetracyclin and drugs of the tetracyclin family, for example, tetracyclin, oxytetracyclin, democlocyclin, methacyclin, doxycyclin, and minocyclin; quinolones, quinoline and quinoline-like drugs, such as, for example, naladixic acid, cinoxacin, norfloxacin, ciprofloxacin, ofloxicin, enoxacin, and pefloxacin; antimicrobial peptides, including but not limited to polymixin B, colistin, and bacatracin, as well as other antimicrobial peptides such as defensins, magainins, cecropins, and others, provided as naturally-occurring or as the result of engineering to make such peptides resistant to the action of pathogen-specific proteases and other deactivating enzymes; other antimicrobial drugs, including vancomycin, rifampicin, metronidazole, ethambutol, pyrazinamide, sulfonamides, isoniazid, and erythromycin.

In another embodiment the drug is an anti viral drug, including but not limited to acyclovir, gangeyclovir, azidothymidine, cytidine arabinoside, ribavirin, amantadine, iododeoxyuridine, poscarnet, and trifluridine.

In another embodiment, the drug is an anti fungal drug including, but not limited to: nystatin, amphotericin, flucytosine, ketoconazole, miconazole, itraconazole, fluconazole, griseofulvin, clotrimazole, econazole, butoconazole, ciclopirox olamine, haloprogin, tolnaftate, naftifine, amphoteracin B, triazoles, papulocandins, pneumocandins, echinocandins, polyoxins, nilikomycins, pradimicins, benanomicins, natarnycin, sulconazole nitrate, terbinafine HCl, terconazole, tioconazole and undecenoic acid.

In another embodiment, the drug is a parasiticide, including, but not limited to: albendazole, amphotericin B, benznidazole, bithionol, chloroquine HCl, chloroquine phosphate, clindamycin, dehydroemetine, diethylcarbamazine, diloxanide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtlmox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide.

For certain applications, a combination of drugs is carried together on the phage carrier. By means of a non-limitative example, aminoglycoside antibiotic drugs may be used as linkers for increasing the drug-carrying capacity of the phage and/or the solubility of other hydrophobic drugs, as described hereinbelow. Thus, for example, an aminoglycoside antibiotic drug (e.g. kanamycin) may be conjugated to the phage via a labile bond, and a second antibiotic drug (e.g. chloramphenicol) may be linked to the aminoglycoside via a second labile bond. In such a case where the aminoglycoside is tethered to the phage by a labile linker, as is the drug linked to the aminoglycoside, both may be released at or within the target cell, allowing additive or synergistic effect of the drugs.

Linkers and Conjugation Methods

In another embodiment, the bacteriophage is conjugated to a drug via a linker. In one embodiment, the linker is a stable linker. In another embodiment, the linker is a labile linker, allowing controlled release of the drug at the target site. In another embodiment, the drug is conjugated to the bacteriophage in an inactive prodrug form, and released as an active drug upon the cleavage of the linker at the target site. As used herein, the term "prodrug" denotes a species that exerts reduced pharmacological activity compared to the active compound. Preferably, the prodrug or precursor form exerts significantly reduced, or more preferably, negligible, pharmacological activity in comparison to the "native" or parent form. In another embodiment, the bacteriophage is covalently linked to the drug via the linker.

According to various embodiments, the labile linker may be enzyme-cleavable, acid-labile, or comprise a disulfide bond. In one embodiment, the release of the drug is facilitated by an enzymatic activity present on the surface of the target cell. In another embodiment, the release of the drug is facilitated by an enzymatic activity present inside the target cell. In yet another embodiment, the release of the drug is facilitated by a combination of enzymatic activities and physiological conditions (e.g. reduced pH, reducing conditions) present inside an intracellular compartments of the target cell. In yet another embodiment, the release of the drug is facilitated by an enzymatic activity present in bodily fluids such as serum. In a further embodiment, the release of the drug is facilitated by the administration of an exogenous enzyme. The release of the drug may be facilitated by various enzymes, including, but not limited to proteases, peptidases, esterases, amidases, glycosidases, lipases and the like. In a different embodiment, the release of the drug is facilitated by acidic pH. Methods for generating acid-labile linkers and prodrugs thereof are available in the art, for example see U.S. Pat. Nos. 6,030,997, 4,631,190, 4,997,913 and 5,140,013.

In another embodiment, the release of the drug is facilitated by an enzyme encoded by a nucleic acid delivered to the target cell by the bacteriophage. Methods for using bacteriophages to deliver genes and express them in prokaryotic or eukaryotic cells are known in the art, as will be discussed hereinbelow.

The coat proteins of a bacteriophage, preferably a filamentous bacteriophage, may be conjugated to a drug using heterobifunctional crosslinking reagents. An exemplary conjugation method is described in Examples 1 and 2 herein. Other methods for chemical conjugation are available in the art, for example by using heterobifunctional linkers including, but not limited to N-succinimidyl 3-(2-pyridyl dithio)propionate (SPDP), m-maleimidobenzoyl-N-hydroxysulfosuccinimide ester, and N-succinimidyl-(4-iodoacetyl)amino-benzoate (See, e.g., published UK Pat. App. Nos. GB 2268492, 2253626, and 2257431). Such heterobifunctional crosslinking reagents can also be used to link the drug to the coat proteins of the bacteriophage via a linker such as a peptide, a polypeptide, a peptide derivative, an oligonucleotide, a lipid, a glycolipid, an oligosaccharide and the like.

It should be explicitly understood, that the linker may also comprise non-covalent bonds either within the linker, or between the linker and the phage and/or the drug. Thus, for example, such linkers and/or drugs may be conjugated to the bacteriophage by means of an avidin/biotin complex. As used herein, "avidin" or "avidin peptide" refers to an avidin molecule, a streptavidin molecule, or a fragment or variant thereof that binds to biotin with an affinity that is approximately the same (i.e., within 10%) or greater than the affinity with which streptavidin binds to biotin. According to this embodiment, the bacteriophage is modified to express on its surface avidin or a portion thereof that selectively binds to biotin with the requisite binding affinity. Modification of the bacteriophage to express avidin is most easily accomplished by inserting the nucleic acid encoding avidin or a functionally active portion thereof into the bacteriophage genome such that the avidin or avidin portion is expressed on the bacteriophage surface. In this manner, an avidin-expressing bacteriophage is produced which serves as an intermediate for attachment of a biotinylated drug or ligand to the bacteriophage surface. Alternatively, avidin or a functionally active portion thereof can be chemically coupled to the bacteriophage surface using standard cross-linking chemistries, such as those described above. The avidin-labeled bacteriophage permits non-covalent, yet high affinity, attachment of pre-selected biotinylated drugs or ligands to the bacteriophage surface for targeted drug delivery to the target cell. Alternatively, the bacteriophage can be biotinylated and an avidin-labeled drug or ligand can be used to form the targeted drug bacteriophages conjugates described herein. The term "conjugated" thus explicitly includes both covalent and non-covalent links between the phage and the drug molecules.

In another embodiment, the bacteriophage is conjugated to other moieties modulating the immunogenicity, pharmacolinetics and/or pharmacodinamics of the bacteriophage-drug conjugate. As a non-limitative example, the bacteriophage-drug conjugate may be pegylated (i.e. conjugated to polyethylene glycol), resulting in reduced immunogenicity (see, for example, US patent application 2004/0161431). Such conjugations may be done prior or following the conjugation to the drug, and typically involve a different conjugation method than that used for conjugating the drug to the bacteriophage. For example, drugs are conjugated to an amino group of the coat protein while surface-modifiers are be conjugated to a thiol group engineered into the coat protein, by methods well known in the art. Such dual conjugation chemistries may also be used for conjugating a plurality of drugs to the bacteriophage.

In other embodiments, the linker is a branched linker or a dendrimer. The term "dendrimer" refers to a three-dimensionally branched, multi-branched compound, and generally refers to all of hyper-branched polymer having a low regularity and dendrimers having a high regularity.

In certain embodiments, a branched linker suitable for linking drugs to the bacteriophage carrier by means of chemical conjugation contains at least two reactive residues that may be used for conjugation. In one embodiment, the residues are selected from the group consisting of amine, carboxyl, hydroxyl and sulfhydryl residues. In certain preferable embodiments, the branched linker has high water solubility, and is thus useful for conjugating hydrophobic drugs.

Figure 13:
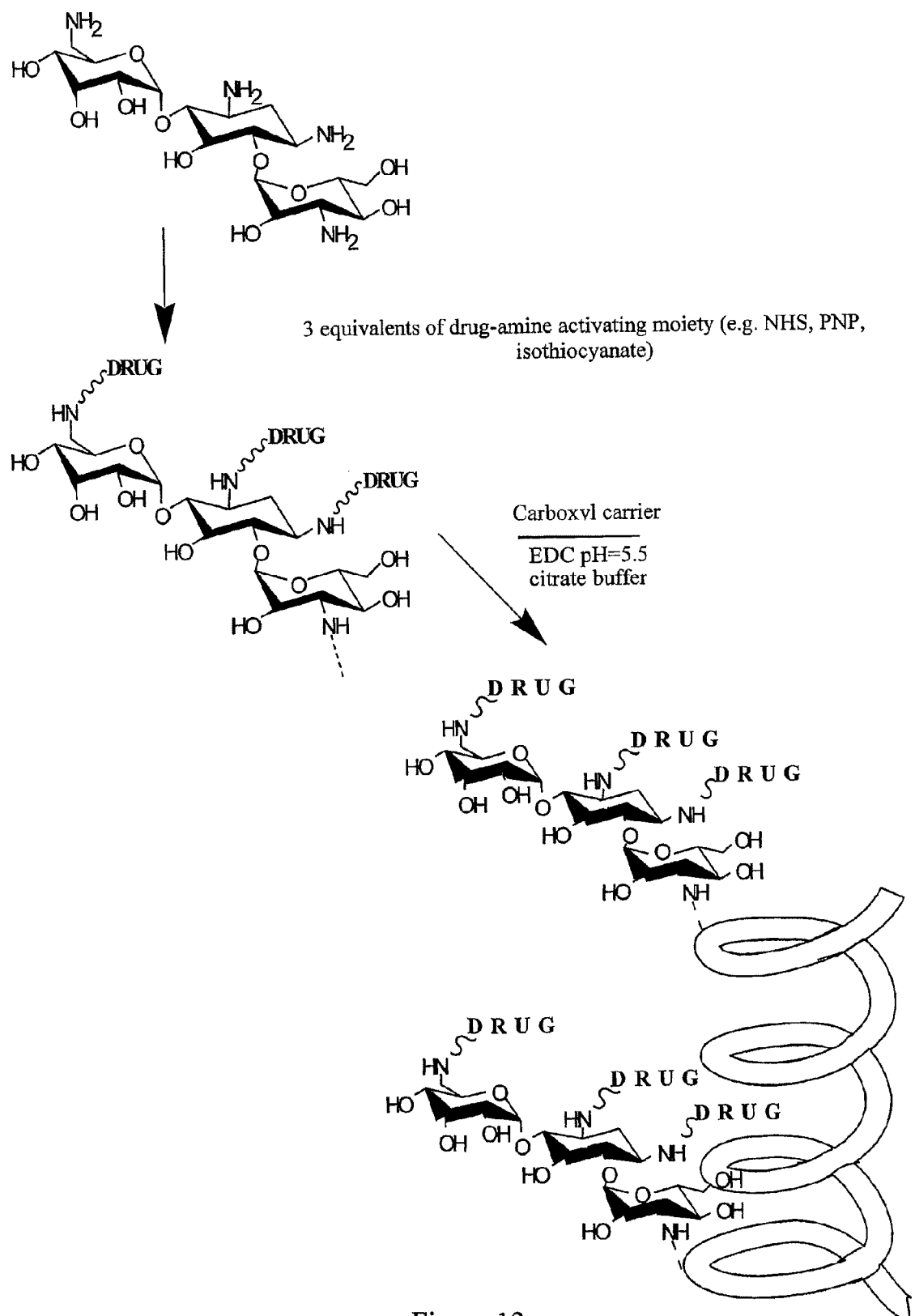
FIG. 13. Scheme of the first method for aminoglycoside-mediated linking of a drug to a bacteriophage carrier. The conjugation (and solubilization of the otherwise poorly soluble drug) is achieved by initial conjugation of hydrophobic drug to the aminoglycoside (kanamycin is presented as an example) followed by EDC conjugation to free carboxyl residues of the bacteriophage carrier.

In one particular embodiment, the linker is an aminoglycoside. The aminoglycoside antibiotics are highly hydrophilic substances, which are naturally produced by the actinomycetes. Most of the molecules in the group comprise multiple amino sugars. The aminoglycosides vary in the form and quanta of amine residues within the molecules, which range between 1-7 amine residues per molecule. The chemical structure of the aminoglycoside antibiotic drug kanamycin, which comprises three amine sugars and four amine residues, is illustrated in FIG. 13.

As demonstrated herein, the use of aminoglycoside linkers provides for enhancing drug carrying capacity and allows conjugation of poorly soluble drugs at a high drug/phage ratio.

According to certain embodiments of the present invention, amplification of the drug-carrying capacity of the targeted drug carriers is facilitated by chemical conjugation of a single amine from an aminoglycoside molecule to a carboxyl residue of the carrier, thereby converting the single carboxyl residue to an amine branched linker.

Preferably, suitable aminoglycoside molecules have two or more reactive residues. Exemplary aminoglycosides include, but are not limited to, hygromycin, kanamycin, gentamycin, amikacin, neomycin, pardomycin, tobramycin and viomycin.

By means of a non-limitative example, amine conjugation methods well-known in the art may be used to conjugate aminoglycosides to the phage carrier and to the drug molecules, including, but not limited to, NHS chemistry, paranitophenyl phosphate (PNP) chemistry, isothiocyanate chemistry and N-(3-dimethylaminopropyl)-N'-ethycarbodiimide (EDC) chemistry. Non-limitative examples of such conjugation processes are presented in Example 8 and FIG. 13.

In other embodiments, the linker, or a component thereof, may be displayed on the phage as a result of genetic modification. In certain embodiments, a peptide linker may be fused to a coat protein of a bacteriophage, to which the drug may be linked by means of chemical conjugation or genetic modification. By means of a non-limitative example, a peptide comprising a side chain suitable for chemical conjugation of the drug (e.g. a cysteine residue suitable for thiol chemistry) and a protease cleavage site (e.g. the di-peptide Phe-Lys cleavable by endosomal Cathepsin-B) is fused to the N' of a coat protein of the phage, such that the drug is released upon internalization of the phage.

Ligands and Target Cells

In another aspect, the invention provides a bacteriophage-drug conjugate displaying an exogenous targeting moiety that selectively binds a target molecule on a target cell. The term displaying an "exogenous targeting moiety" as used herein encompasses targeting moieties that are not naturally expressed or displayed on a bacteriophage coat, which are either expressed by a genetically-modified bacteriophage or linked to the bacteriophage by means of genetic modification, chemical conjugation or both. The targeting moiety and its manner of expression or linkage is designed to facilitate the bacteriophage-drug conjugate to selectively bind a target cell. This term further includes a targeting moiety comprising a ligand conjugated to the phage that binds non-covalently to a second targetor molecule capable of binding the target cell.

In one embodiment, the bacteriophage is genetically modified to selectively bind a target cell. In another embodiment, the genetic modification results in the display of a ligand on the phage coat. In a preferred embodiment, the genetic modification is in the form of a targeting moiety-coding DNA sequence fused to a gene coding for a coat protein of the phage. Phages that display foreign proteins or peptides as a fusion with a phage coat protein are well known to those familiar with the art. A variety of phages and coat proteins may be used, including, but not limited to: M13 protein m, M13 protein VIII, M13 protein VI, M13 protein VI, M13 protein IX, fd minor coat protein pIII (Saggio et al., 1995; Uppala and Koivunen, 2000), lambda D protein (Sternberg and Hoess, 1995; Mikawa et al., 1996), lambda phage tail protein pV (Maruyama et al., 1994), fr coat protein (WO 96/11947), f29 tail protein gp9 (Lee and Guo, 1995), MS2 coat protein (Heal et al., 1999), T4 SOC, HOC, IPIII and fibritin proteins (Hong and Black, 1993; Efimov et al., 1995; Ren and Black, 1998), PRD-1 gene III, Qb3 capsid protein and p22 tailspike protein (Carbonell and Villaverde, 1996). In the preferred filamentous phage system, a large array of vectors are available (see Kay et al., 1996; Berdichevsky et al., 1999; Benhar, 2001). In a preferred embodiment, the ligand is displayed by its fusion to the major coat protein (protein VIII) of a filamentous phage. In another preferred embodiment, the ligand is displayed by its fusion to the minor coat protein (protein III) of a filamentous phage.

In another embodiment, the targeting moiety is linked to the phage by the methods of chemical conjugation described above for chemically conjugating drugs to bacteriophages. Ligands to be chemically conjugated may be isolated from natural sources or made synthetically, such as by recombinant means or chemical synthesis, by methods well known to the skilled artisan.

An isolated nucleic acid sequence encoding a targeting moiety can be obtained from its natural source, either as an entire (i.e., complete) gene or a portion thereof. A nucleic acid molecule can also be produced using recombinant DNA technology (e.g., polymerase chain reaction (PCR) amplification, cloning) or chemical synthesis. Nucleic acid sequences include natural nucleic acid sequences and homologs thereof, including, but not limited to, natural allelic variants and modified nucleic acid sequences in which nucleotides have been inserted, deleted, substituted, and/or inverted in such a manner that such modifications do not substantially interfere with the nucleic acid molecule's ability to encode a functional targeting moiety of the present invention. A nucleic acid molecule homolog can be produced using a number of methods known to those skilled in the art (see, for example, Sambrook et al., 1989). Methods for inserting foreign coding sequences into a phage gene are well known (see e.g., Sambrook et al., 1989; Brent et al., 2003). Certain non-limitative examples of genetically modifying a bacteriophage to express exogenous targeting moieties are presented in the Examples below.

Alternatively, a targeting moiety of the invention may be synthesized using any recombinant or synthetic method known in the art, including, but not limited to, solid phase (e.g. Boc or f-Moc chemistry) and solution phase synthesis methods. The term "analogs" relates to peptides or polypeptides obtained by replacement, deletion or addition of amino acid residues to the sequence, optionally including the use of a chemically derivatized residue in place of a non-derivatized residue, as long as they retain their capability to bind the desired target molecule.

The targeting moiety is any biological substance endowed with specific binding properties towards a selected target cell. In one preferred embodiment, the targeting moiety is an antibody-based moiety, including, but not limited to: monoclonal antibodies, polyclonal antibodies, and antibody fragments such as recombinant antibody fragments, single-chain antibodies (scFv), single antibody variable domains, and the like (Borrebaeck, 1995; Lo, 2003). Single-chain antibodies are small recognition units consisting of the variable regions of the immunoglobulin heavy ($V_H$) and light ($V_L$) chains which are connected by a synthetic linker sequence. Single antibody domain proteins (dAbs) are minimized antibody fragments comprising either an individual $V_L$ domain or an individual $V_H$ domain.

Methods of generating monoclonal and polyclonal antibodies are well known in the art. Antibodies may be generated via any one of several known methods, which may employ induction of in vivo production of antibody molecules, screening of immunoglobulin libraries, or generation of monoclonal antibody molecules by continuous cell lines in culture. These include, but are not limited to, the hybridoma technique, the human B-cell hybridoma technique, and the Epstein-Barr virus (EBV)-hybridoma technique. Antibody fragments may be obtained using methods well known in the art, including, but not limited to by proteolytic hydrolysis of the antibody or by expression in *E. coli* or mammalian cells (e.g., Chinese hamster ovary (CHO) cell culture or other protein expression systems) of DNA encoding the fragment. (Fab')2 antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody. An Fv is composed of paired heavy chain variable and light chain variable domains. This association may be non-covalent. Alternatively, as described hereinabove, the variable domains may be linked to generate a single-chain Fv by an intermolecular disulfide bond, or alternately such chains may be cross-linked by chemicals such as glutaraldehyde. Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. In addition, techniques may be utilized to change a "murine" antibody to a "human" antibody, without altering the binding specificity of the antibody.

In another preferred embodiment, the targeting moiety is a peptide endowed with binding specificity towards the target cell (linear, circularly constrained or cyclic) or a short peptide selected from a library of short peptide sequences that is endowed with binding specificity towards the target cell (Kay et al., 1996). Methods for constructing libraries and using them for screening for ligands having an affinity to a selected target molecule or cell are known in the art (see, e.g. Kay et al., 1996). See also certain non-limitative methods of using peptide libraries to select targetor peptides having an affinity to a desired target in the Examples hereinbelow.

In other embodiments, the ligand is a polypeptide, a carbohydrate, a lipid, a glycolipid, a saccharide, a nucleic acid and the like, which is able to selectively bind a target molecule on a target cell. For instance, the ligand may include known ligands of cell surface receptors, or any natural or synthetic derivative thereof.

In another embodiment, the bacteriophage-drug conjugate displays a ligand capable of binding a targetor that selectively binds a target molecule on a target cell. Examples of such ligands include, but are not limited to: the ZZ domain derived from *Staphylococcus aureus* protein A, which binds an antibody that is endowed with binding specificity towards the target cell (Nilsson et al., 1987), and avidin or streptavidin based sequences which may bind biotinylated antibodies endowed with binding specificity towards the target cell, as described above. Such ligands may be used for the construction of a kit for generating a targeted bacteriophage-drug conjugate, comprising: (i) a bacteriophage-drug conjugate displaying a ligand capable of binding a targeting moiety that selectively binds a target molecule on a target cell; and (ii) instructions for linking the targeting moiety to the ligand. The kit may also contain reagents for linking the targeting moiety to the ligand, a targeting moiety to be linked to the ligand, and optionally other tools or containers. These kits may be used to linking a bacteriophage-drug conjugate of the invention to the desired targeting moiety (e.g. an antibody directed to a target molecule of choice), enabling a selective delivery of the drug to any target cell of interest.

In certain particular embodiments, the ZZ domain is fused to a coat protein of the phage. In various embodiments, the ZZ domain may be fused to the major coat protein, or, in alternate embodiments, the minor coat protein of a filamentous bacteriophage. A bacteriophage may display the ZZ domain on all its coat proteins or on a portion of its coat proteins.

According to certain embodiments, the invention provides a filamentous bacteriophage displaying the ZZ domain on some or all copies of its minor coat protein. In one embodiment, the ZZ domain is fused to the N terminus of the coat protein. In certain particular embodiments, the modified coat protein has an amino acid sequence as set forth in SEQ ID NO:1 and analogs thereof, as long as the analog retains its ability to serve as a functional coat protein and bind to IgG Antibodies. In other particular embodiments, said coat protein is encoded by a nucleotide sequence having a nucleic acid sequence as set forth in SEQ ID NO:2 and homologs thereof, as long as the homolog retains its ability to encode a functional coat protein and bind to IgG Antibodies. This bacteriophage may be linked to a drug as detailed above and used as a targeted drug carrier of the invention. Thus, according to a particular embodiment of the present invention there are provided bacteriophage-drug conjugates wherein the bacteriophage has a coat protein having an amino acid sequence as set forth in SEQ ID NO:1 and analogs thereof.

The ligand is chosen according to the specific drug, target cell and disorder to be addressed. For certain applications, ligands are chosen such that they are internalized by the target cell upon binding the target molecule, thereby enabling the internalization of the drug-carrying bacteriophage. Methods of constructing and selecting for internalizing phages are known in the art (see, for example, Becerril et al., 1999, Kassner et al., 1999, Poul and Marks, 1999, Larocca and Baird, 2001, Larocca et al., 2001, Urbanelli et al., 2001, U.S. Pat. Nos. 6,451,527, 6,448,083, and International Application WO 98/05344). For other applications, the bacteriophage-drug conjugate is not internalized, and the drug either penetrates the cell upon the cleavage of the linker, or act in the extracellular compartment.

The ligands used in the context of this invention do not necessarily retain any of their in vivo biological activities, other than binding a target molecule on a target cell. However, it may be desirable in certain contexts that a ligand exerts certain of its biological activities. In certain embodiments, the ligand may act as an agonist, or alternatively as an antagonist, upon binding a cell surface receptor.

As the drug molecules are conjugated to the outer surface of the phage, its delivery to the target cell does not necessitate the internalization of the bacteriophage-drug-conjugate. Therefore, ligands capable of binding a large array of target molecules on various target cells may be used for preparing the conjugates of the present invention.

The ligand displayed by the targeted bacteriophage-drug conjugate of the invention is selected so as to facilitate selective binding of the conjugate to a target cell involved in a disease or disorder in a subject in need thereof. In one embodiment, the target cell is a bacterial cell. In another embodiment, the target cell is a fungal cell. In another embodiment, the target cell is a yeast cell. In another embodiment, the target cell is a unicellular parasite (e.g. protozoa) cell. In another embodiment, the target cell is a multicellular parasite (e.g. helminth) cell. In another embodiment, the target cell is a virus-infected mammalian cell. In another embodiment, the target cell is a mammalian cell infected by a microorganism. In another embodiment, the target cell is a mammalian cell infected by a parasite. In another embodiment, the target cell is a tumor cell. In another embodiment, the target cell is a cell that supports tumor growth such as tumor neovasculature. In another embodiment, the target cell is a diseased cell such as an outgrowth of muscle cells at a restenotic plaque, an epithelial cell in psoriasis, an immune cell involved in the development of an autoimmune disease, and any diseased or malfunctioning cell that may be targeted through a distinct surface molecule. In some cases, the cells to be treated may be selected based on cosmetic rather than strictly medical criteria, e.g. destruction of adipocytes to treat obesity.

In one embodiment, the subject in need thereof is a human subject. In another embodiment, the subject in need thereof is a mammal. In another embodiment, the subject in need thereof is a non-mammalian animal.

Pharmaceutical Compositions

The invention provides pharmaceutical compositions comprising the bacteriophage-drug conjugates of the invention. The term pharmaceutical composition as used herein also includes compositions suitable for veterinary use. Anti-microbial compositions for decontamination or prevention of bacterial infestation are further contemplated.

Pharmaceutical compositions according to the present invention can be prepared by admixing a quantity of a purified targeted drug-carrying bacteriophage with a pharmaceutically acceptable carrier. For example, the compositions of the present invention may be administered in the form of injectable compositions. A typical composition for such purpose comprises a pharmaceutically acceptable carrier. For instance, the composition may contain human serum albumin and phosphate buffer containing NaCl. Other pharmaceutically acceptable carriers include aqueous solutions, non-toxic excipients, including salts, preservatives, buffers and the like, as described in Remington's Pharmaceutical Sciences, 15$^{th}$ Ed. Easton: Mack Publishing Co. pp 1405-1412 and 1461-1487 (1975) And The National Formulary XIV., 14$^{th}$ Ed. Washington: American Pharmaceutical Association (1975), the contents of which are hereby incorporated by reference. Examples of non-aqueous solvents include propylene glycol, polyethylene glycol, vegetable oil and injectable organic esters such as ethyloleate. Aqueous carriers can include water, alcoholic/aqueous solutions, saline solutions, parenteral vehicles such as sodium chloride, Ringer's dextrose, and the like. Intravenous vehicles include fluid and nutrient replenishers. Preservatives include antimicrobials, anti-oxidants, chelating agents and inert gases. The pH and exact concentration of the various components of the bacteriophage pharmaceutical compositions of the invention can be adjusted according to routine known in the art. See Goodman And Gilman's The Pharmacological Basis For Therapeutics (7th ed.).

Due to the stability of phages in the gastrointestinal tract, they are also suitable as drug delivery vessels in oral formulations, e.g. for the treatment of systemic infections. Oral compositions will generally include an inert diluent or an edible carrier and may be compressed into tablets or enclosed in gelatin capsules. Tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring. When the dosage unit form is a capsule, it can contain, in addition to material of the above type, a liquid carrier such as a fatty oil. Alternatively, the pharmaceutical compositions of the present invention can be in the form of liposomes, lipophilic microcapsules, dendrimers or the like for oral administration. Those skilled in the art are capable of preparing the bacteriophage compositions of the present invention in the form of a lipophilic microcapsule, a dendrimer or a liposome using conventional techniques known in the art. The bacteriophage-drug preparations of the invention may also be administered with food.

The skilled artisan also is capable of providing a bacteriophage composition that can be administered intranasally, rectally, transdermally, topically, or other known routes of administration of medicaments. Solutions or suspensions used for parenteral, intradermal, subcutaneous, or topical application can include any of the following components: a sterile diluent, such as water for injection, saline solution, fixed oil, polyethylene glycol, glycerin, propylene glycol or other synthetic solvent, anti-microbial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. Parental preparations can be enclosed in ampoules, disposable syringes or multiple dose vials made of glass, plastic or other suitable material.

The phage can also be mixed with other active materials that do not impair the desired action or with materials that supplement the desired action.

Therapeutic Use

The conjugates and complexes provided herein are useful in the treatment and prevention of various diseases, syndromes and disorders, including, but not limited to: hyperproliferative disorders such as restenosis; other smooth muscle cell diseases; tumors, such as melanomas, ovarian cancers, neuroblastomas, pterygii, secondary lens clouding and the like; autoimmune diseases; and infectious diseases caused by bacteria, viruses, yeast, fungi, and parasites. Other disorders that may be treated by the conjugates of the invention include, but are not limited to, disorders such as psychotropic and psychiatric disorders, metabolic disorders cholesterol balance disorders and diabetes. As used herein, "treatment" means any manner in which the symptoms of a condition, disorder or disease are ameliorated or otherwise beneficially altered. Treatment also encompasses any pharmaceutical use of the compositions herein. As used herein, "amelioration" of the symptoms of a particular disease or disorder refers to any lessening, whether permanent or temporary, lasting or transient, that can be attributed to or associated with administration of the composition.

In one embodiment, the targeted bacteriophage-drug conjugates of the present invention may be used to treat tumors. In these diseases, cell growth is excessive or uncontrolled, Tumors suitable for treatment within the context of this invention include, but are not limited to, breast tumors, gliomas, melanomas, prostate cancer, hepatomas, sarcomas, lymphomas, leukemias, ovarian tumors, thymomas, nephromas, pancreatic cancer, colon cancer, head and neck cancer, stomach cancer, lung cancer, mesotheliomas, myeloma, neuroblastoma, retinoblastoma, cervical cancer, uterine cancer, and squamous cell carcinoma of skin. For such treatments, ligands can be chosen to bind to cell surface receptors that are generally preferentially expressed in tumors (e.g. MUC-1 and Tac). Through delivery of the compositions of the present invention, unwanted growth of cells may be slowed or halted, thus ameliorating the disease. The methods utilized herein specifically target and kill or halt proliferation of tumor cells having receptors for the ligand on their surfaces.

The bacteriophage-drug conjugates may also be used to treat or prevent atherosclerosis and stenosis, a process and the resulting condition that occurs following angioplasty in which the arteries become reclogged. Generally, treatment of atherosclerosis involves widening a stenotic vascular lumen, permitting greater blood flow and oxygenation to the distal tissue. Unfortunately, these procedures induce a normal wound healing response in the vasculature that results in restenosis. Of the three components to the normal vascular response to injury, thrombosis, elastic recoil and smooth muscle cell proliferation, anti-thrombotics/platelet inhibitors and vascular stents effectively address acute/subacute thrombosis and elastic recoil, respectively. However, no therapy can modify the vascular remodeling that is due to proliferation of smooth muscle cells at the lesion, their deposition of extracellular matrix and the subsequent formation of a neointima. Accordingly, bacteriophage-drug conjugates could be used to deliver therapeutic drugs that would inhibit restenosis.

In one embodiment of the invention, the compositions are useful for treating autoimmune diseases, i.e. diseases in which the immune system functions inappropriately and reacts to a component of the host as if it were, in fact, foreign. Such a response results in an autoimmune disease, in which cells of the host's immune system attacks the host's own tissue. Autoimmune diseases that may be treated by the bacteriophage-drug conjugates of the invention include, but are not limited to: multiple sclerosis, autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis) autoimmune hepatitis and rheumatoid arthritis.

In certain embodiments, the compositions of the present invention may be used to treat angiogenesis-dependent diseases. In these diseases, vascular growth is excessive or allows unwanted growth of other tissues by providing blood supply. These diseases include angiofibroma, arteriovenous malformations, arthritis, atherosclerotic plaques, corneal graft neovascularization, delayed wound healing, diabetic retinopathy, granulations due to burns, hemangiomas, hemophilic joints, hypertrophic scars, neovascular glaucoma, nonunion fractures, Osler-weber syndrome, psoriasis, pyogenic granuloma, retrolental fibroplasia, scleroderma, solid tumors, trachoma, and vascular adhesions. By inhibiting vessel formation (angiogenesis), unwanted growth may be slowed or halted, thus ameliorating the disease. In a normal vessel, a single layer of endothelial cells lines the lumen, and growth of the vessel requires proliferation of endothelial cells and smooth muscle cells.

The compositions of the present invention can also be used to treat a subject having an infection, including, but not limited to: a bacterial infection, a viral infection, a yeast infection, a fungal infection, and a parasitical infection. Suitable bacteriophage-containing compositions can be prepared that will be effective in killing, obliterating or reducing the quantity of any of the microorganisms or parasites using the guidelines presented above.

The compositions of the present invention preferably are administered intravenously, intranasally, orally, topically etc., in an amount and for a period of time effective to treat the infection. The expression "treating an infections", as it is used throughout this description, denotes either (i) killing or obliterating sufficient microorganisms or parasites to render the microorganisms or parasites ineffective in infecting the host, or (ii) reducing a sufficient quantity of microorganisms or parasites so as the render the microorganisms or parasites more susceptible to treatment using conventional antibiotics or drugs.

Determining an effective amount of host-specific, non-toxic purified bacteriophage-drug conjugate composition to be administered in accordance with the present invention entails standard evaluations. An assessment in this regard would generate data concerning bioavailability, absorption, metabolism, serum and tissue levels and excretion, as well as microorganism or parasite levels, markers, and cultures. The appropriate dosage and duration of treatment can be ascertained by those skilled in the art using known techniques.

According to one embodiment, bacteriophage-drug conjugate compositions prepared according to the present invention can be used to reduce but not entirely obliterate the population of microorganisms or parasites, thereby rendering the infectious focus more susceptible to other chemotherapeutic antibiotics and thus reducing in combination therapy duration, side effects, and risks of the latter. Thus, for example, the bacteriophage pharmaceutical compositions of the present invention can be used in combination with known antibiotics such as aminoglycosides, cephalosporins, macrolides, erythromycin, monobactams, penicillins, quinolones, sulfonamides, tetracycline, and various anti-infective agents. Those skilled in the art can refer to the Physician's Desk Reference, $50^{th}$ Ed (Medical Economics (1996)), or similar reference manuals for a more complete listing of known antibiotics which could be used in combination with the bacteriophage compositions. For example, a bacteriophage composition effective against various strains of *Staphylococcus* could be used in combination with a cephalosporin such as Keflex™ or Keftab™ (both from Cephalexin). Those skilled in the art, using the guidelines provided herein, are capable of designing an effective treatment regimen by either using the bacteriophage-drug conjugate composition alone or using a bacteriophage-drug conjugate composition in combination with antibiotics.

Similarly, bacteriophage-drug conjugate compositions for the treatment of other infectious or non-infectious diseases and conditions, such as those described above, may be used alone or in combination with one or more therapeutic agents, administered together or separately, e.g., prior to, concurrently with or following the administration of the pharmaceutical compositions the invention. For example, bacteriophage-drug conjugate compositions for the treatment of neoplasms can be used in combination with additional chemotherapeutic drugs or other anti-cancer agents well known in the art.

In one aspect, the invention provides a method of treating a disease or disorder in a subject in need thereof, comprising administering to the subject a therapeutically effective amount of a pharmaceutical composition comprising a bacteriophage-drug conjugate of the invention.

In one embodiment, the subject is a mammal. In another embodiment, the subject is human. In another embodiment, the subject is a non-mammalian animal.

In another aspect, the invention provides a method of treating a bacterial infection or infestation, comprising contacting the bacteria with a bacteriophage-drug conjugate of the invention. In one embodiment, the bacteriophage is capable of infecting and killing the bacteria. In another particular embodiment, the bacteria belong to the Staphylococcus family (e.g. *Staphylococcus Aureus*).

In yet another aspect, the invention provides a method of treating a disease or disorder in a subject in need thereof, comprising administering to the subject a therapeutically effective amount of a pharmaceutical composition comprising a bacteriophage-drug conjugate, wherein the bacteriophage comprises a nucleic acid molecule comprising an exogenous nucleic acid sequence that is expressible in the target cell. As used herein, "exogenous genetic material" refers to a polynucleotide (e.g., nucleic acid or oligonucleotide), either natural or synthetic, that is not naturally found in a bacteriophage, or if it is naturally found in the bacteriophage, it is not transcribed or expressed at biologically significant levels by the bacteriophage. "Exogenous genetic material" includes a non-naturally occurring polynucleotide that can be transcribed into an antisense RNA, as well as all or part of a "heterologous gene" (i.e., a gene encoding a protein which is not expressed or is expressed at biologically insignificant levels in a naturally-occurring bacteriophage). Thus, for example, the present invention embraces the introduction into a target cell of an expression cassette including a recombinant gene containing an inducible promoter operably linked to a coding sequence of a therapeutic polynucleotide or oligonucleotide. In the preferred embodiments, the exogenous genetic material of the bacteriophage can be both transcribed and translated in the target cell. For suitable methods of generating such vectors and expression cassettes, see e.g. Sambrook et al., 1989; Ausubel et al., 1994.

In one embodiment, the exogenous nucleic acid sequence encodes an enzyme that is capable of cleaving the linker connecting the drug to the bacteriophage, thereby releasing the drug. In another embodiment, the exogenous gene encodes an antimicrobial peptide, an antibiotic, a toxin, an enzyme or a cytotoxic agent.

Methods for the construction and use of vectors for phage mediated gene delivery to both prokaryotic and eukaryotic cells are known in the art; see, for example, WO 2004/062677, WO 98/05344 and U.S. Pat. No. 6,448,083, among many others.

In another aspect, the invention is directed to the use of a bacteriophage-drug conjugate of the invention for the preparation of a pharmaceutical composition for the treatment of a disease or disorder as specified above.

The following examples are presented in order to more fully illustrate some embodiments of the invention. They should, in no way be construed, however, as limiting the broad scope of the invention.

EXAMPLES

Materials and methods: All the chemicals used were of analytical grade and were purchased from Sigma (Israel). Unless stated otherwise, reactions were carried out at room temperature (about 25° C.).

Preparation of Phages for Drug Conjugation. Filamentous Phages were Routinely propagated in DH5-α F'cells using standard phage techniques as described (Enshell-Seijffers et al., 2002). Phages were usually recovered from overnight 1 liter cultures of carrying bacteria. The bacteria were removed by centrifugation and the phage-containing supernatant was filtered through a 0.22 μm filter. The phages were precipitated by addition of 20% (w/v) polyethylene glycol 8000 PEG/2.5M NaCl followed by centrifugation as described (Enshell-Seijffers et al., 2002). The phage pellet was suspended in sterile miliQ double-distilled water at a concentration of $10^{13}$ cfu/ml and stored at 4° C.

Example 1

Preparation and Evaluation of Chloramphenicol-Linker Adduct

Chloramphenicol (CAM) was chemically modified in two synthetic steps to create an ester bond between CAM and a linker (originated in glutaric-anhydride). The linker CAM prodrug complex was activated for further lysine conjugation by the NHS procedure as done in biotinylation procedure. The overall conjugation scheme is described in FIG. 1.

In the first step, the primary OH group of chloramphenicol was reacted with glutaric anhydride to create an ester linkage. The reaction was done in a solution of dry THF (5, 6, 7, 8-tetrahydrofolic acid) and DMAP (γ-(dimethylamino) propanol) with equal molar equivalents of the three reactants: triethylamine, glutaric anhydrid and chloramphenicol. The result of this step was a chloramphenicol-linker adduct. In the second step, the free carboxyl group of the chloramphenicol-linker adduct was activated to allow subsequent linkage to amine groups such as on lysines. Specifically, the reaction was done in a solution of $CH_2Cl_2$ (di-chloromethane) with a combination of the reactants listed: of DCC (1,3-dicyclo-hexylcarbodiimide, carbodicyclohexylimide); NHS (N-Hydroxysuccinimide) and the chloramphenicol-linker adduct from the first step at molar equivalents 1.5; 1.5; 1, respectively.

The chloramphenicol-prodrug did not inhibit the growth of susceptible bacteria at concentrations up to ×100 of the free chloramphenicol $IC_{50}$, showing that, indeed, the chloramphenicol was concerted to a prodrug.

The release of CAM from the linker was found to be dependent on serum esterases that cleave the ester bond between CAM and the linker (that is connected to the primary hydroxyl). The CAM-linker adduct was found to be stable at pH values between 6-8. However, the CAM could be liberated by incubation in the presence of horse serum as a source for esterases. To test the CAM release rate, a reverse phase HPLC analysis was done based on the fact that elution time of free CAM is about 9 min while the CAM-linker adduct is eluted about 16 min after sample injection into a reverse phase C18 column. This was done as follows: reverse phase HPLC was used to measure the chloramphenicol release rate following the incubation of chloramphenicol-prodrug in 10% or in 99% horse serum, or without serum, all in PBS. A reverse phase C-18 column was used on a LabChrom L7400 MERCK HITACHI machine with acetonitrile:water (30:70) in the mobile phase at 1 ml/min flow rate. Under these conditions, free chloramphenicol is eluted 9 min after sample loading while the intact chloramphenicol-prodrug is eluted 16 min after sample loading. The % of released chloramphenicol was calculated by dividing the area of the 9 min peak by the total peak area of all relevant peaks and multiplying by 100.

Figure 2A:
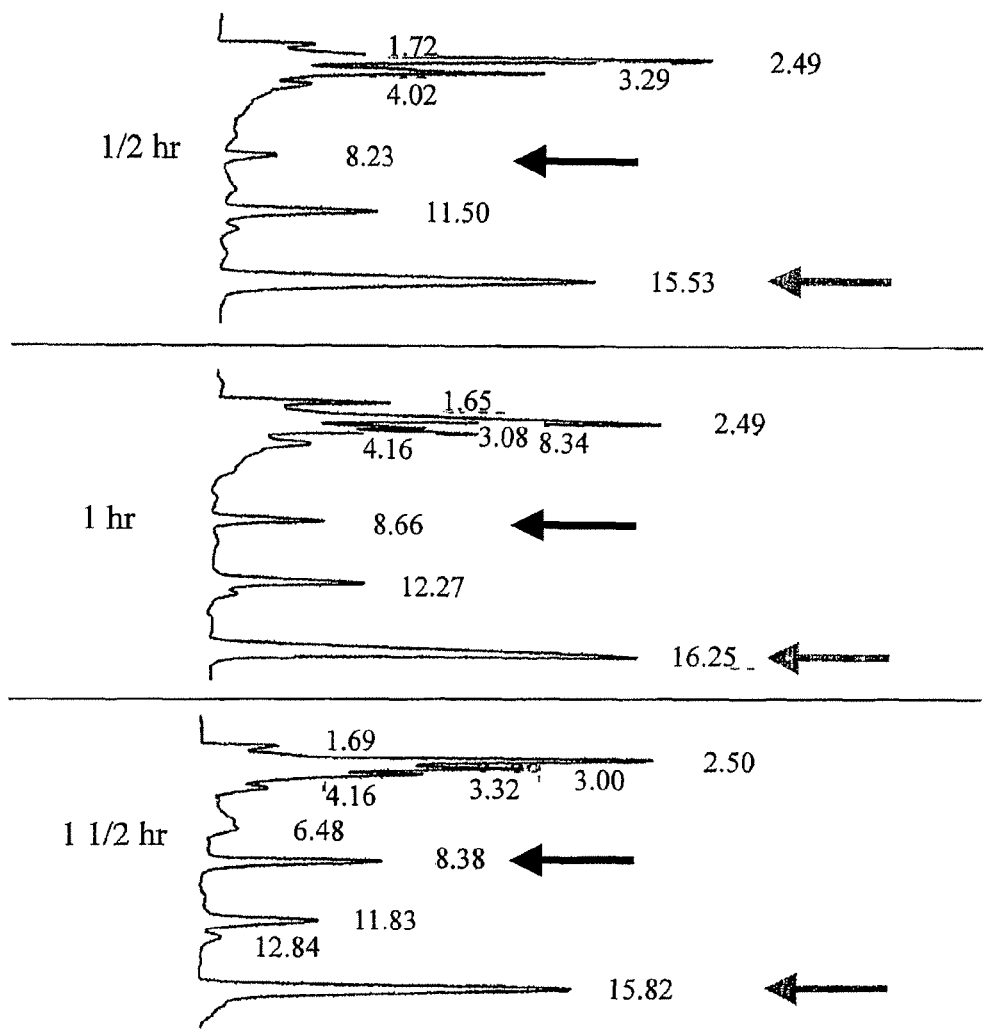
FIG. 2. CAM release rate from its linker in 99% horse serum. (A) Reverse phase HPLC was used to measure the breakdown rate following the incubation for the indicated time periods in 99% horse serum at 37° C. Free chloramphenicol (marked by black arrows) is eluted 9 min after sample loading while intact chloramphenicol-linker adduct (marked by gray arrows) is eluted 16 min after sample loading. (B) release rate of chloramphenicol from its linker in 10% horse serum (gray bars) or without serum (in PBS, black bars) was evaluated by HPLC as in A, the % released chloramphenicol was calculated by dividing the area of the 9 min peak by the total peak area of all relevant peaks.
Figure 2B:
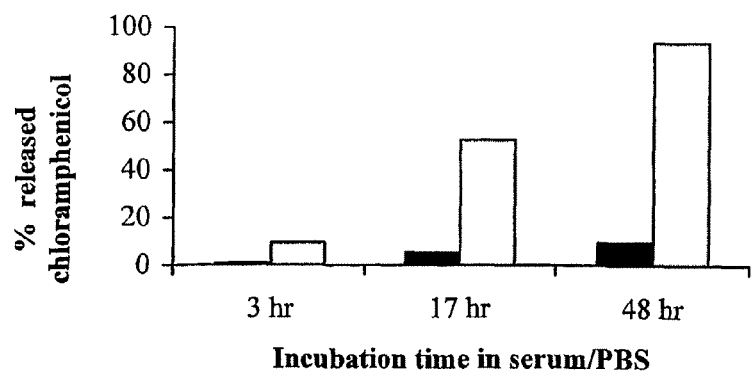

The amount of the released CAM was calculated from the peaks area. As shown in FIG. 2A, about 15% of CAM was released from the linker after 1 hr incubation in 99% horse serum at 37° C. with linear kinetics. A similar release rate was found after the chloramphenicol-prodrug was conjugated to phages followed by release with serum. The stability of the chloramphenicol-prodrug was evaluated by a more prolonged incubation, where release rate was monitored over 48 hours in the presence of 10% horse serum, or without serum. As shown in FIG. 2B, the release rate followed the same linear kinetics as with the 99% serum (after correcting for the concentration difference). The spontaneous hydrolysis rate of the ester bond in PBS alone was less than 5% over the entire 48 h period.

Example 2

Figure 3A:
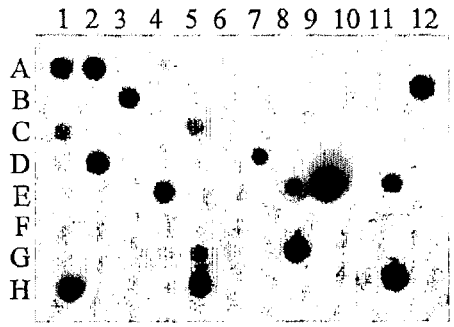
FIG. 3. Identification of peptide-displaying phages that bind H23 scFv. Dot-Blot analysis of phages from the first (A) and second (B) Reverse DIP selection cycles. Affinity-selected phages were applied as dots onto nitrocellulose filters and reacted with 10 µg/ml HumH23-MBP-scFv. A mouse anti-MBP mAb and HRP-conjugated goat anti mouse antibodies were used as first and secondary antibodies, respectively. The membranes was developed using ECL reagents and exposure to x-ray film (Mazor et al., 2005).
Figure 3B:
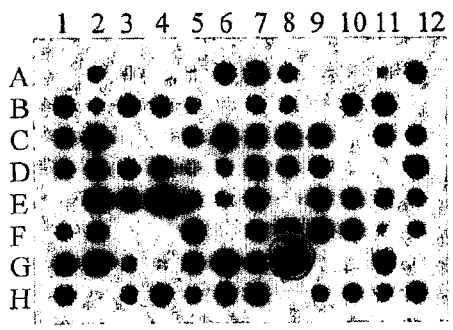

Filamentous Phage as a Targeted Drug Carrier using a Surrogate Antibody-Antigen System In the set of experiments described below, the pathogen (target cell) is an *E. coli* strain of the serotype O78, an avian pathogen causing septicemia (Babai et al., 1997). A model targeting moiety-target system for the application of targeted phages as drug carriers was constructed. In this model, the humanized single-chain antibody (scFv) H23 was introduced into on *E. coli* O78 cells for surface display, using our recently described Lpp-ompA' system (Benhar et al., 2000; Mazor et al., 2005). The scFv-displaying cells are the target cells while the targeted drug carriers were H23-specific phages that display a 7 amino acids (aa) peptide that was found as the epitope bound by the H23 scFv. The phage was isolated by panning a 7-mer linear library of random peptides displayed using a 8+8 system (Enshell-Seijffers et al., 2001) on H23 scFv displaying *E. coli* cells, a process we named "reverse DIP" as described (Mazor et al., 2005). The ability of the peptide to bind H23 scFv is demonstrated in FIG. 3. The phage clone MucC5 that was used in the present study is circled.

The particular peptide on phage MucC5, with the sequence QRGPDTRPVIAAG (shown here with 3 p8 flanking residues an each side of the 7 mer peptide, SEQ ID NO:5) is not supposed to be harmed by the conjugation process (that targets primarily epsilon amines of lysine residues) since it lacks lysine residues. The filamentous phage major coat protein p8 is a 60 residues protein with each monomer containing 8 lysines. The phage coat is assembled by wrapping of the single-stranded DNA genome by 2500-3000 p8 molecules (the number may further defer according to the size of the packaged genome (Smith et al., 1998), and may be manipulated based on modifications or mutagenesis of the coat protein (Malik et al., 1996; Sidhu, 2001; Held and Sidhu, 2004)). Of these 8 lysines, about 3 may be available to chemical conjugation. Since a single M13 phage contains about 3000 copies of Protein VIII it means a theoretical potential of ~10000 drug molecules to a single phage, as was evaluated by conjugating biotin to intact phages (Nakamura et al., 2001; Nakamura et al., 2002).

Figure 4:
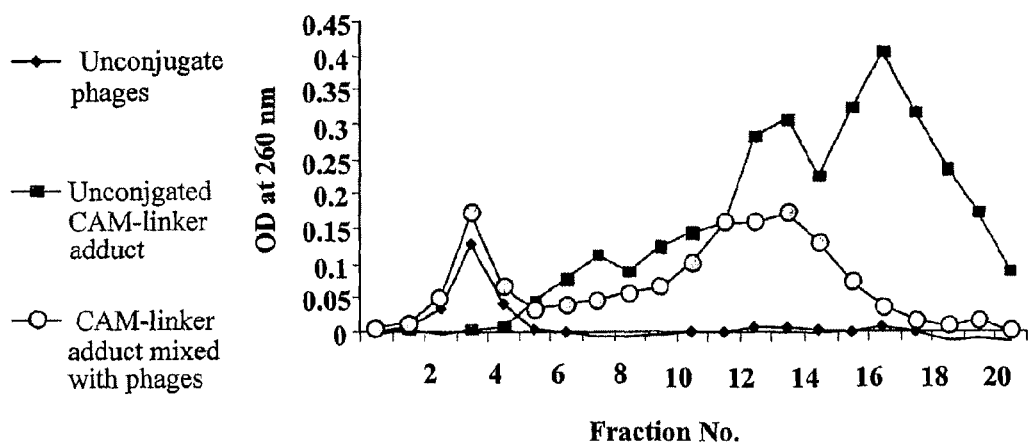
FIG. 4. Separation of conjugated phages from unconjugated drug. Gel filtration chromatography was used to separate the CAM conjugated phages from the excess of unconjugated CAM-linker adduct. A 10 cm long, 1 cm diameter Sepharcyl S200 column was developed at a flow rate of 2 ml/min. The analyzed materials were loaded in 2 ml into the column and 2 ml fractions were collected.

The CAM-linker adduct (example 1) was conjugated to the phages by mixing an excess amount of NHS activated CAM with about $10^{13}$ phages in 1 ml of phosphate buffered saline at 4° C. overnight. Three consecutive conjugation cycles were performed. The reaction mixture was separated by gel filtration using a 10 cm long, 1 cm diameter Sephacryl S200 column that was developed at 2 ml/min with PBS and 2 ml fractions were collected. Unconjugated phages and free CAM-liker adduct were analyzed separately for comparison. As shown in FIG. 4, the phages eluted in the first five 2 ml fractions while the free CAM-linker adduct eluted starting at the $6^{th}$ fraction. By releasing the phage conjugated drug and ultrafiltration we found that 10,000-30,000 molecules of CAM were linked to each phage. Phages that eluted in fraction 3 were collected for further use.

Figure 5:
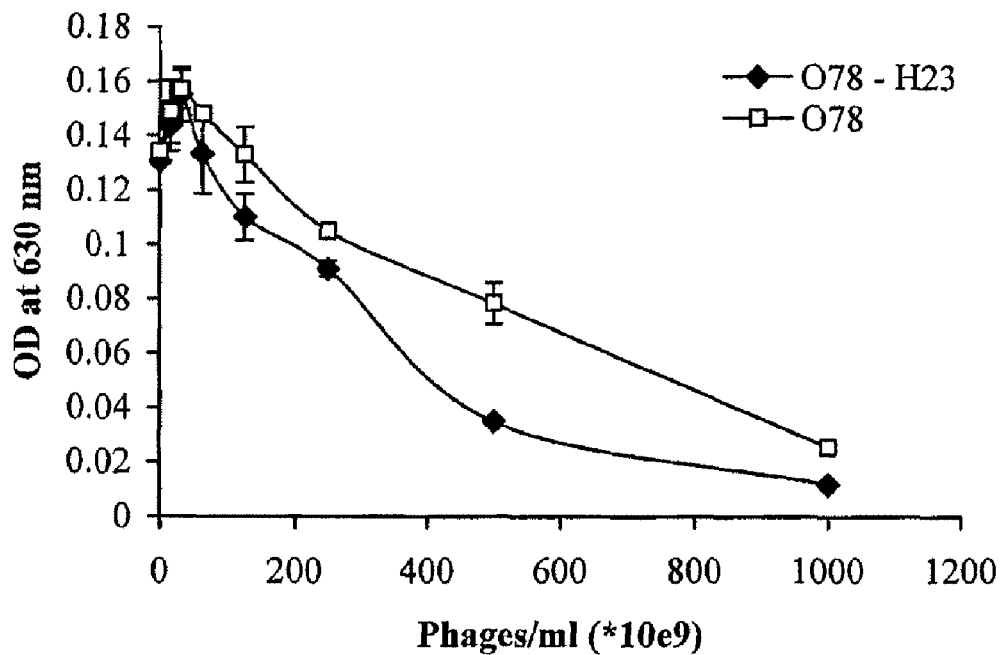
FIG. 5. Phage targeting effect evaluated in *E. coli* O78H23 antibody model system. Phages of clone MucC5 (displaying the H23 epitope, peptide QRGPDTRPVIAAG, SEQ ID NO:5 on the major coat protein p8) were conjugated to CAM and mixed at various ratios with ~$10^7$ O78 *E. coli* cells that display the H23 single-chain antibody (scFv) (empty diamonds) on their surface or with non displaying cells (full squares) used as negative control. Control cells were grown without adding serum. Cells were incubated in 100 ml of SOB medium containing 25% horse serum in a flat-bottom 96 well plate shaking at 200 RPM for 6 hours. Growth was recorded after 6 hr at 600 nm.

To test the targeting effect of the CAM-conjugated phages, a dilution of CAM-phages were added to an identical number of O78 E. coli (non-target) bacteria in comparison with same number of O78H23(Fv)-displaying (target) bacteria. As shown in FIG. 5, a clear effect could be seen at a low dilution while at higher dilution the targeting effect vanished. It can be seen that in low dilution of phages there are visible effect of targeting while in higher dilutions this effect was lost. This demonstrates that the phages carry and release enough drug to retard the growth of the cells on one hand, and a targeting effect by more efficient killing of the target cells compared to the cells that do not express the target molecule.

Example 3

Filamentous Phage as a Targeted Drug Carrier using a Genuine Cell-Surface Molecule as a Target Two random peptide libraries, a 7-mer and a disulfide-bond constrained 12-mer combinatorial phage-peptide were designed on the fth1 'type 88' expression vector (Enshell-Seijffers et al., 2001), each contains >$10^9$ random peptides displayed on the N-terminus of the major coat protein p8 of the Fd filamentous bacteriophage. E. coli K91K cells (Smith and Scott, 1993) were used for phage propagation. The peptide library phages were affinity selected on E. coli O78 cells, as follows: cells were grown in 2XYT medium supplemented with 12.5 µg/ml tetracycline at 30° C. The cells ($10^9$ cells) were collected by centrifugation and washed twice with 1 ml of chilled PBST. Washed cells were re-suspended with 1 ml 1% (v/v) non-fat milk in PBS containing $10^{11}$ cfu of the peptide library phages and left on ice for 1 h. The cells were then washed three times (1 ml each wash) with PBST and three times with PBS (Benhar and Reiter, 2001). The selecting O78 cells were then mixed with $10^9$ of K91K E. coli cells in 1 ml that were grown in 2XYT medium supplemented with 50 µg/ml kanamycin with vigorous shaking at 37° C. These cells express the F' pilus that serves as the phage receptor and are infected by the selected phage output. The mixed cultures was incubated for 30 min at 37° C. without shaking followed by incubation for 30 min at 37° C. with gentle shaking that enables the selected phages to infect the K91K bacteria. Aliquots were taken for determination of phage panning output and the rest of the culture was either plated on 2XYT plates containing 20 µg/ml tetracycline and 50 µg/ml kanamycin to obtain single colonies for immunoscreening or amplified to obtain a phage stock to be used as input for the next selection cycle.

Randomly selected single colonies of K91K cells infected with phage output after the fourth cycle were picked and used to inoculate 200 µl of 2XYT medium supplemented with 20 µg/ml tetracycline per well in U-bottom 96-well plates. After overnight growth at 37° C. with shaking at 150 rpm, the plates were centrifuged and the supernatant from each well was mixed at 1:1 ratio with PBST and tested for binding to O78 cells that were coated onto well of 96/well polystyrene ELISA plates (about $10^7$ cell/well). The K12 E. coli strain MC4100 and Salmonella (ST1) were used as a negative control.

Figure 6:
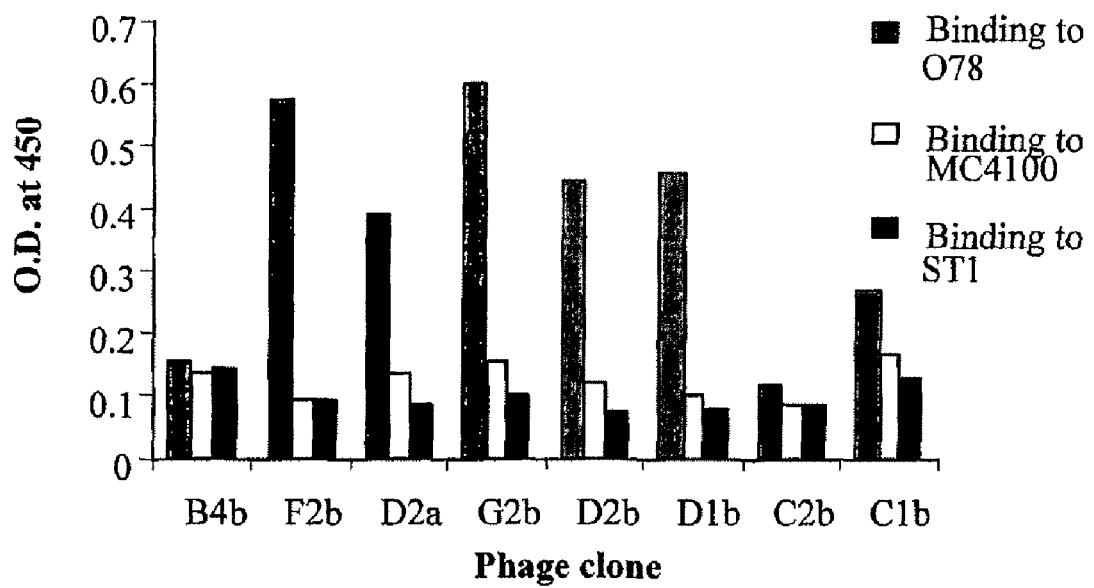
FIG. 6. Binding of O78 *E. coli* cells in ELISA. Affinity-selected peptide-displaying phages ($10^{10}$/well) were applied onto wells that were coated with ~$10^7$ bacteria in PBS. After extensive washing, bound phages were detected using HRP-conjugated anti M13 antibodies followed by developing with the HRP substrate TMB. The reaction was stopped with 1M $H_2SO_4$ and color was recorded at 450 nm.

Eight phage clones were identified as specific O78 binders using phage ELISA essentially as described (Benhar and Reiter, 2001). As shown in FIG. 6, they bound the O78 bacteria but not the control bacteria.

Phages C2b and D1a, together with the H23 scFv-binding phage MucC5 were chosen to assess the targeting effect of CAM-conjugated O78-specific phages. The phages were conjugated as described above. $10^8$ O78-H23(scFv) displaying bacteria were mixed with $5 \times 10^{12}$ phages in 110 µl and rotated for 1 hr at room temperature. The cells were collected by centrifugation and the unbound phages were removed. The cells were re-suspended in 200 µl horse serum and left at room temperature for 3 hr. The cells were then diluted into 3 ml of SOB medium and grown at 37° C. shaking at 250 RPM in 13 ml polystyrene tubes. Bacterial growth was determined by reading absorbance at 600 nm.

Figure 7:
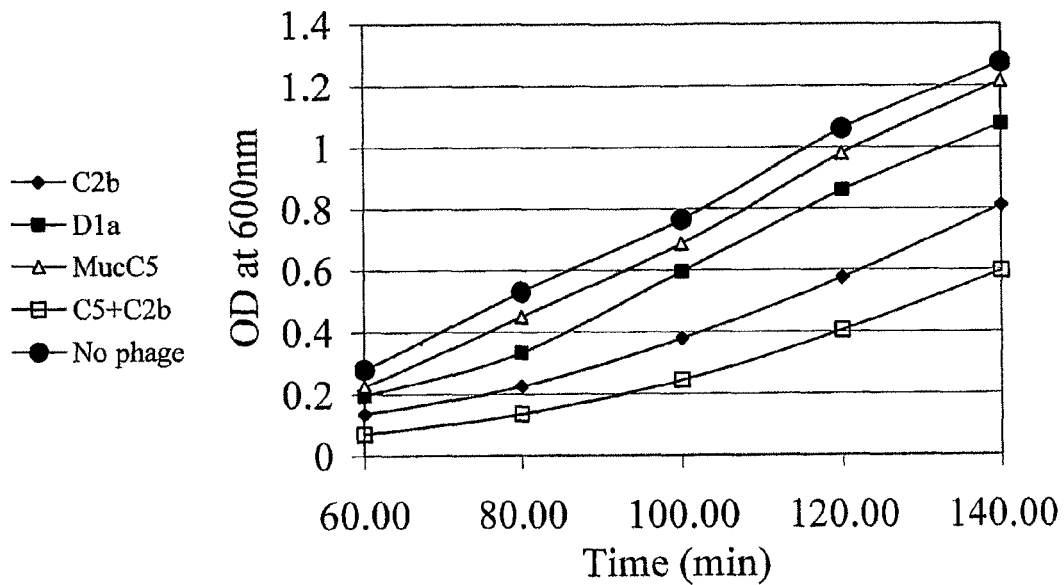
FIG. 7. Phage targeting effect on "genuine" target cells. Growth curves of O78-H23(scFv)-displaying *E. coli* cells treated with various CAM-conjugated phages. The indicated time is the recording following dilution of the treated phages into 3 ml SOB medium.

As shown in FIG. 7, the growth of the bacteria was retarded following treatment with the CAM-conjugated O78-specific phages and by the H23(scFv)-specific phage MucC5. Moreover, when treated with a combination of C2b (O78-specific) and MucC5 (H23(scFv)-specific) phages, the growth was retarded even more, suggesting that a combination of drug-carrying phages may be advantageous for treatment.

Example 4

Controlled Drug Release from CAM Conjugated Phages by Added Esterases

Figure 8:
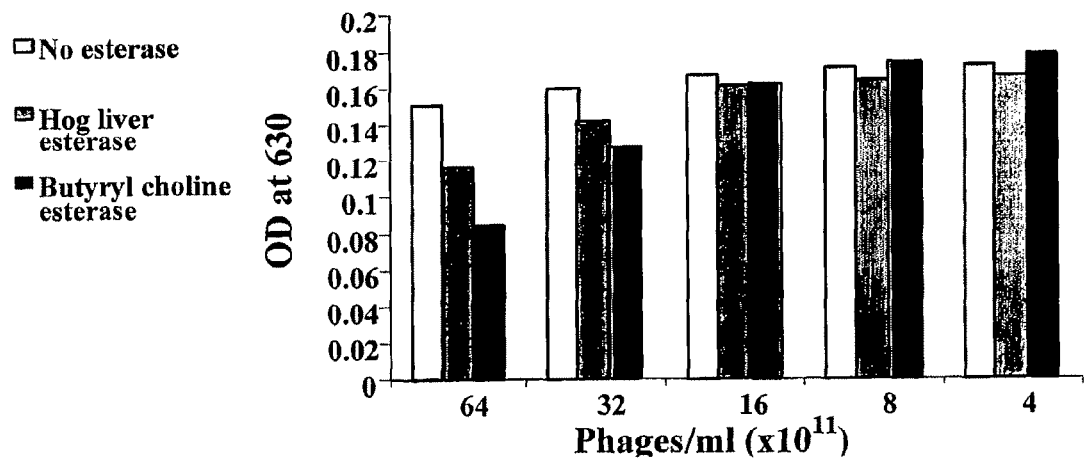
FIG. 8. Inhibition of bacterial growth by controlled CAM release. Growth of *E. coli* O78 cells treated with various CAM-conjugated phages in the presence of esterases.

In the above-described examples, the CAM that was linked to the linker via a labile ester bond was released in the presence of horse serum. To demonstrate controlled release of the drug, the following experiment was carried out: the effect of added CAM-conjugated phages on the growth of O78 E. coli cells was tested in the absence of serum. Rather, Hog liver esterase (Sigma, Israel) or butyryl-choline esterase (Sigma, Israel) were added. 100 µl of culture was placed in each well of a flat bottom 96/well plate. The culture contained about $10^7$ bacteria/ml, serial dilution of CAM-conjugated O78-specific peptide-displaying phages of clone C2 (see above) in SOB medium. To the bacteria/phage mix we added the esterase to a final concentration of 12 units/ml, or only buffer as control. The plates were shaken at 37° C., 240 RPM and growth was recorded after 5 hr at 630 nm as described above. As shown in FIG. 8, the addition of both esterases resulted in release of the CAM that retarded the growth of the O78 E. coli bacteria.

Example 5

Isolation of *Staphylococcus aureus*-Binding Phages

A phage peptide display library of about $10^9$ clones of disulfide-bond constrained 12-mer random peptides was affinity selected on live SA cells as follows: we used a random 12-mer peptide combinatorial phage-display library, based on the fth1 'type 88' expression vector (Enshell-Seijffers et al., 2001), which contains >$10^9$ random clones. In this library, the peptides are displayed on the N-terminus of the major coat protein p8 of the Fd filamentous bacteriophage. E. coli K91K cells (Smith et al., 1993) were used for phage propagation. The library phages were affinity selected on *Staphylococcus aureus* (SA) cells, as follows: SA were grown in Tryptic soy broth (TSB, Difco, USA) medium at 37° C. The cells were collected by centrifugation and washed twice with 1 ml of chilled phosphate-buffered saline (PBS) containing 0.05% (v/v) tween 20 (PBST). $10^9$ washed cells were re-suspended with 1 ml of 1% (v/v) non-fat milk in PBS containing $10^{11}$ cfu of peptide library phages and left on ice for 1 h. The cells were then washed three times (1 ml each wash) with PBST and three times with PBS (Benhar et al., 2002). The selecting SA cells were then mixed with $10^9$ of E. coli K91K cells in 1 ml that were grown in 2XYT medium (Benhar et al., 2002) supplemented with 50 µg/ml kanamycin with vigorous shaking at 37° C. The mixed cultures was incubated for 30 min at 37° C. without shaking followed by incubation for 30 min at 37° C. with gentle shaking that enables the selected phages to infect the K91K *E. coli* bacteria. Aliquots were taken for determination of phage output and the rest of the culture was either plated on 2XYT plates (Benhar et al., 2002) containing 20 µg/ml tetracycline and 50 µg/ml kanamycin to obtain single colonies for immunoscreening, or amplified to obtain a phage stock to be used as input for the next affinity selection cycle.

After the fourth affinity selection cycle, randomly selected single colonies of K91K cells infected with phage output were picked and used to inoculate 200 µl of 2XYT medium supplemented with 20 µg/ml tetracycline per well in U-bottom 96-well plates. After overnight growth at 37° C. with shaking at 150 rpm, the plates were centrifuged and the phage-containing supernatant from each well was mixed at 1:1 ratio with PBST and tested for binding to SA cells by phage ELISA.

Following four selection cycles, random clones were screened for binding to immobilized SA cells by phage ELISA, as follows: SA cells were coated onto wells of 96/well polystyrene ELISA plates as described below. Serial dilutions of the tested phages were added to the wells and allowed to bind for 1 h. Following the 1 h incubation with phages, the plates were washed x3 with PBST and HRP-conjugated rabbit anti M13 antibody (Amersham Biosciences, USA) diluted x5000 in PBST was added (100 µl/well) and incubated for 1 h. The plates were washed x3 with PBST and development was done with 100 µl/well of the HRP substrate TMB (Dako, USA). Following color development, the reaction was terminated with 50 µl/well of 1M $H_2SO_4$. The color signal was recorded at 450 nm.

ELISA plates (Flat bottom, Nunc, Sweden) were coated with bacteria as follows: cells from a fresh overnight culture were collected by centrifugation and suspended in PBS at about $10^8$ cells/ml. An aliquot of 100 µl of the cell suspension was applied into each well of the plate that was spun in a centrifuge at 4000 RPM for 5 min at 4° C. The supernatant was carefully removed and 100 µl of 3% glutaraldehyde in PBS were added to each well and left to fix the cells for 1 h. Next, the plate was blocked with 3% (w/v) skim milk powder in PBS and 5% rabbit serum (a crucial step for blocking the IgG binding capacity of SA because of their own protein A). The *E. coli* strain O78 cells were used as a negative control.

Figure 9A:
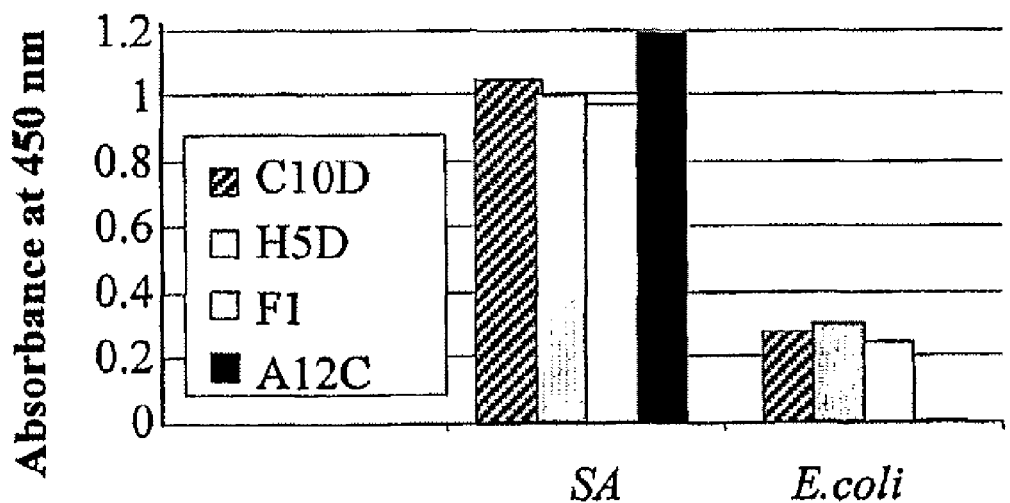
FIG. 9. Binding of peptide-displaying phages to SA (*Staphylococcus aureus*). (A) Affinity-selected peptide-displaying phages ($1 \times 10^{10}$/well, names shown in inset) were applied onto wells pre-coated with ~$10^7$. After extensive washing, bound phages were detected using HRP-conjugated anti M13 antibodies followed by development with the HRP substrate TMB. Optical density was recorded at 450 nm. (B) Phage-peptide A12C targeting effect evaluated in SA (*Staphylococcus aureus*) native system. Absorbance at 450 nm.

The binding signals of four such clones and the deduced sequences of the peptides they display are shown in FIG. 9A and Table 1:

TABLE 1

Sequences of the peptides displayed on SA-specific binders and the number of duplicates that were identified in the initial screen by phage ELISA. Lysines that may be vulnerable to amine conjugation chemistry are in bold.

| Clone name | SEQ ID NO: | Sequence | No. of duplicates identified | OD on SA cells | OD on *E. coli* cells |
|---|---|---|---|---|---|
| C10D | 6 | SPGHYWDTKLVD | 3 | 1.05 | 0.275 |
| H5D | 7 | TYFPTMGTSFKI | 4 | 1.003 | 0.3 |
| F1 | 8 | TFLRGPSSPLVS | 2 | 0.97 | 0.24 |
| A12C | 9 | VHMVAGPGREPT | 1 | 1.2 | 0.007 |

As shown, higher ELISA signals were obtained on the SA target cells in comparison to the control *E. coli* cells. As frequently happens following several affinity selection cycles, some of the clones were isolated more than once Table 1. Phage A12C that yielded the highest binding signal difference between the target to the control cells, and that displays a lysine-less peptide (and should not be harmed by the drug conjugation) was chosen for further evaluation as a targeted drug carrier.

A12C phages were conjugated to the chloramphenicol-prodrug and their capacity to bind SA was compared to non-conjugated phages.

The phages were conjugated as follows: A stock solution of $10^{13}$ CFU/ml phages and a stock solution of 100M chloramphenicol-prodrug were used. A constant molar ratio of $3 \times 10^5$ for the chloramphenicol-prodrug molecules/phage was used. The reaction was mixed overnight. Next, phage precipitates were removed by centrifugation for 15 min at 14,000 RPM at 4° C. in a microfuge. Soluble phages were precipitated with PEG/NaCl as described above.

To evaluate the number of chloramphenicol molecules that could be conjugated to a single phage, we liberated the drug by prolonged incubation with serum and separated the drug from the phages by ultrafiltration, as follows: a similar number of chloramphenicol-conjugated phages as well as non-conjugated phages as a reference were incubated for 48 hr in the presence of 10% Rabbit serum (Sigma, Israel) at 37° C. The phage solutions were ultra-filtered using a 10 kDa cutoff ultrafiltration microcon cartridge (Millipore, USA) to eliminate the phages as well as other large proteins and contaminants. The filtrate optical absorbance was recorded at 280 nm and the number of released chloramphenicol molecules was calculated by using a calibration curve of free chloramphenicol absorbance was recorded at 280 nm. The concentration of the liberated chloramphenicol was calculated by comparing its optical absorbance at 280 nm to a calibration curve. We found (Table 2) that several consecutive conjugation steps are required to achieve a maximal coverage of the phages with drug, at >20000 molecules/phage. However, at this conjugation level, most of the phages were lost due to precipitation. Therefore, a single conjugation cycle resulting in 2000-4000 drug molecules/phage was performed.

TABLE 2 number of chloramphenicol molecules conjugated/phage in consecutive conjugation cycles.

| Conjugation cycle | No. of chloramphenicol molecules/phage |
|---|---|
| 1 | 3600 |
| 2 | 17000 |
| 3 | 24000 |

Figure 9B:
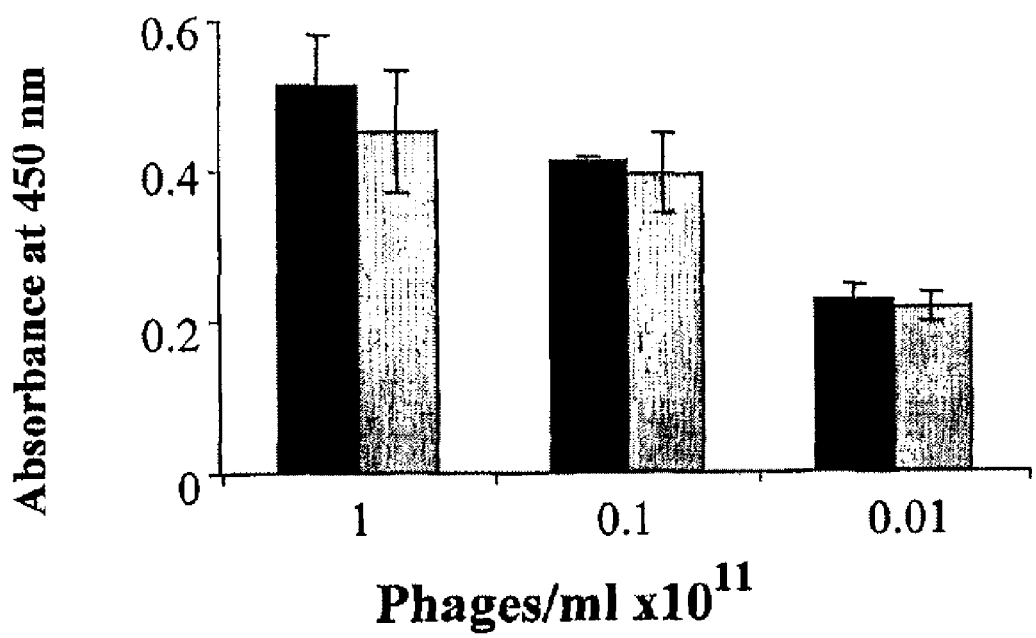

As shown in FIG. 9B, the SA binding capacity of the phages was not affected by drug conjugation.

Example 6

Isolation of ZZ Domain-Displaying Phages

Phage fUSE5-ZZ, for polyvalent display of the ZZ domain on all copies of the P3 minor coat protein was constructed as follows: The IgG-binding ZZ domain (SEQ ID NO:3, encoded by SEQ ID NO:4) was initially cloned for monovalent display on the filamentous phage p3 coat protein as follows: the DNA fragment carrying the ZZ domain open reading frame was recovered by PCR using plasmid pSD-ZZ (Freeman et al., 2004) as template with primers CCGCTT CCATGGTAGACAACAAATTCAACAAAG (SEQ ID NO:10) and GGGTTTA GCGGCCGCTTTCGGCGCCTGAGCATCATTTAG (SEQ ID NO:11). The PCR product was digested with restriction enzymes NcoI and NotI (restriction sites underlined in the primer sequences) and cloned into a vector fragment that was isolated from phagemid vector pCANTAB5E (Berdichevsky et al., 1999) by digestion with the same enzymes. The resulting plasmid was named pCANTAB-ZZ. The IgG-binding ZZ domain was further cloned for polyvalent display on all copies of the filamentous phage p3 coat protein as follows. Initially, phage vector fUSE5 (http://www.biosci.missouri.edu/smithgp/PhageDisplayWebsite/vectors.doc) was modified to accept single chain antibodies as NcoI-NotI fragments. The anti-Tac scFv coding DNA was recovered by PCR using pCANTAB5E-anti-Tac (Benhar et al., 2000) as template with primers AATTTC GGCCGACGTGGCCATGGCCCAGGTCAAACT (SEQ ID NO:12) and TATTCACAAACGAATGGATCC (SEQ ID NO:13). The PCR product was digested with restriction enzymes SfiI and BamHI (restriction sites underlined in the primer sequences) and cloned into a vector fragment that was isolated from fUSE5 DNA by digestion with the same enzymes. The resulting phage vector was named fUSE5-anti-Tac. The ZZ domain was subcloned into the fUSE5 backbone by replacing the NcoI and NotI scFv fragment of fUSE5-anti-Tac with NcoI and NotI scFv ZZ domain fragment of pCANTAB-ZZ, resulting in phage fUSE5-ZZ. The resulting phage p3 protein has an amino acid sequence as set forth in SEQ ID NO:1, and is encoded by a nucleic acid sequence as set forth in SEQ ID NO:2.

Figure 10A:
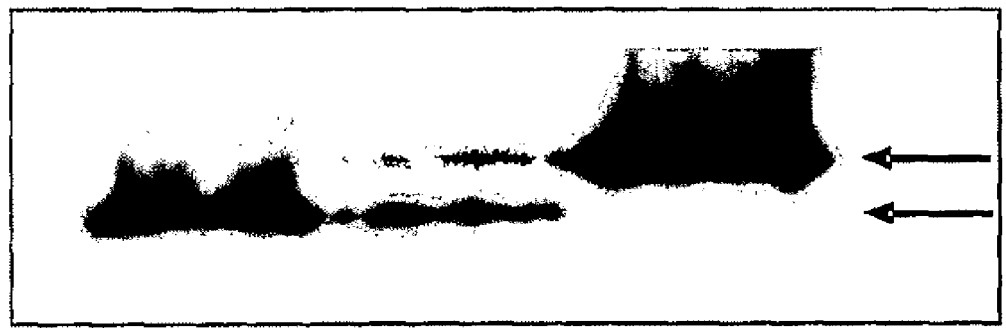
FIG. 10. Evaluation of ZZ domain display on phage and the effect of drug conjugation on the ZZ domain IgG binding capacity. (A) Evaluation of ZZ domain display by an immunoblot. The upper arrow marks the position of the ZZ-P3 fusion, while the lower arrow marks the position of wild-type P3 coat protein. (B) Comparison of the binding capacity of phage displayed ZZ domain to HRP conjugated rabbit IgG that yields a color signal with the substrate TMB at 450 nm. fUSE50ZZ phages were evaluated before conjugation (black bars), following conjugation to the chloramphenicol prodrug (striped bars), or following conjugation to the chloramphenicol prodrug while protected by complexed IgG (gray bars). Error bars represent the standard deviation of the data.

To compare monovalent to polyvalent display of the ZZ domain, an immunoblot analysis was carried out. In the immunoblot we compared the P3 protein of M13KO7 helper phage (where only the WT protein is incorporated in the phage coat), that of pCANTAB-ZZ following its rescue by M13KO7 helper phage (where both the ZZ-fused P3 and the WT protein provided by the helper are incorporated in the phage coat), and fUSE5-ZZ (to determine whether it has only the ZZ-fused P3 incorporated in the phage coat). This was performed as follows: $10^{11}$ phage particles were separated by electrophoresis on a 12% SDS-polyacrylamide gel. The gel was electroblotted onto a nitrocellulose membrane which was developed using an anti P3 monoclonal antibody (Lab collection) followed by an HRP-conjugated rabbit anti mouse antibody (Jackson ImmunoResearch Laboratories, USA). The membrane was developed by using ECL reagents as described. As shown in FIG. 10A, the fUSE5-ZZ phages demonstrated polyvalent display of ZZ on their coat.

The phages were conjugated to the chloramphenicol-prodrug as described in Example 5 and their capacity to bind IgG was evaluated, as follows: IgG binding capacity was evaluated by incubating $10^{12}$ CFU of fUSE5-ZZ phages, before or following conjugation to the chloramphenicol-prodrug, with ×10,000 dilution of HRP-conjugated rabbit anti mouse IgG (Jackson ImmunoResearch Laboratories, USA) in 1 ml PBS for 1 hr. Next, phages and phage-IgG complexes were precipitated with PEG/NaCl as described above. The pellets were suspended in 1 ml of PBS and X3 dilutions were made in an ELISA plate containing 100 µl PBS at each well prior to addition of phages. Development was done by addition of 50 µl the HRP substrate TMB (Dako, USA). Following color development, the reaction was terminated with 50 µl/well of 1M $H_2SO_4$. The color signal was recorded at 450 nm. The possibility of protecting the ZZ domain from conjugation-induced deterioration was evaluated as follows: fUSE5-ZZ was "protected" by complexation with human protein A-purified IgG prior to chloramphenicol conjugation. A total of $10^{13}$ fUSE5-ZZ phages in 1 ml PBS were complexed with 15 µg human IgG for 1 h. Complexation was followed conjugation with the chloramphenicol prodrug as described above. Precipitates were removed by centrifugation for 15 min at 14,000 RPM at 4° C. in a microfuge. Next, the protecting human IgG was released from the ZZ domain by lowering the pH to 2.5 by adding 500 µl of 50 mM Glycine/HCl pH 2.2 (resulting in pH~2.5) and incubating for 20 min. PEG/NaCl precipitation was used to precipitate and separate the fUSE5-ZZ phages from the free human IgG. The IgG binding capacity was evaluated by incubating the phages with HRP-conjugated rabbit anti mouse IgG as described above.

Figure 10B:
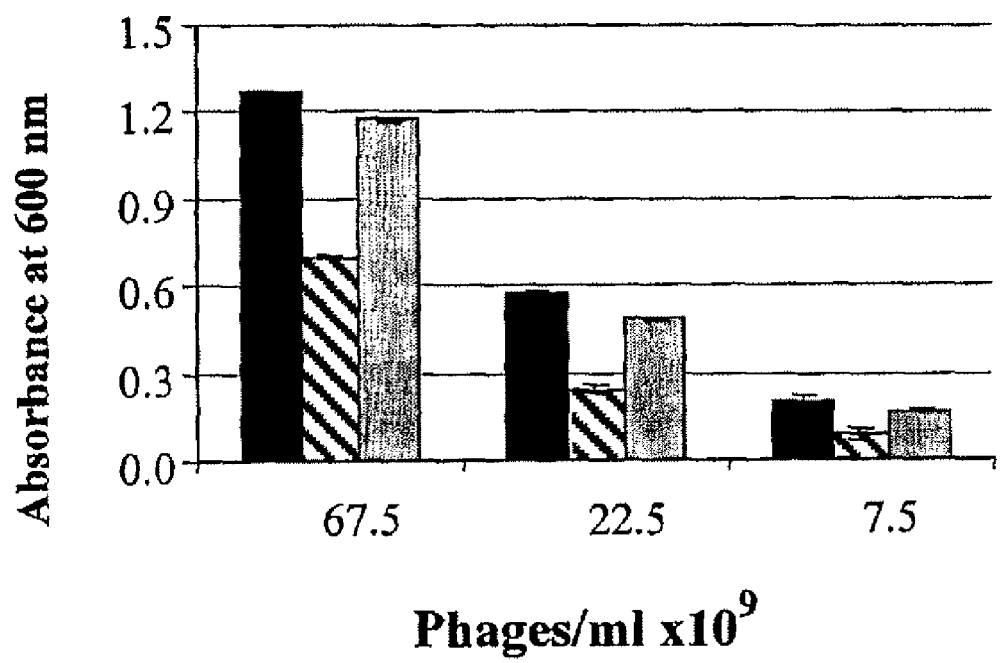

As shown in FIG. 10B, at this conjugation level, the ZZ domain lost about 50% of its IgG binding capacity. However, protection of the ZZ domain could be achieved by complexation with human IgG prior to drug conjugation.

Example 7

The Effect of Targeted Drug-Carrying Phages on the Growth of *Staphylococcus aureus*

Phage A12C was chosen to assess the targeting effect of chloramphenicol-conjugated *S. aureus*-specific peptide-displaying phages. Conjugates were evaluated for their effect on bacterial growth as follows: an overnight bacterial culture was diluted ×100 in PBS. 1 ml of diluted bacteria was collected by centrifugation at 14,000 RPM and pellet re-suspended in 100 µl PBS. 10 µl of this bacterial suspension was mixed with 100 µl of $10^{12}$ phages in ml PBS, and then incubated for 1 hr. The incubation of the cells with the phages was followed by incubation with 50% rabbit serum for 1 hr, after which they were diluted directly into 2 ml of TSB medium 20% rabbit serum in 13 ml tubes shaking at 250 RPM at 37° C. Growth was recorded after dilution into the TSB medium by recording the optical density (OD) at 600 nm.

Figure 11A:
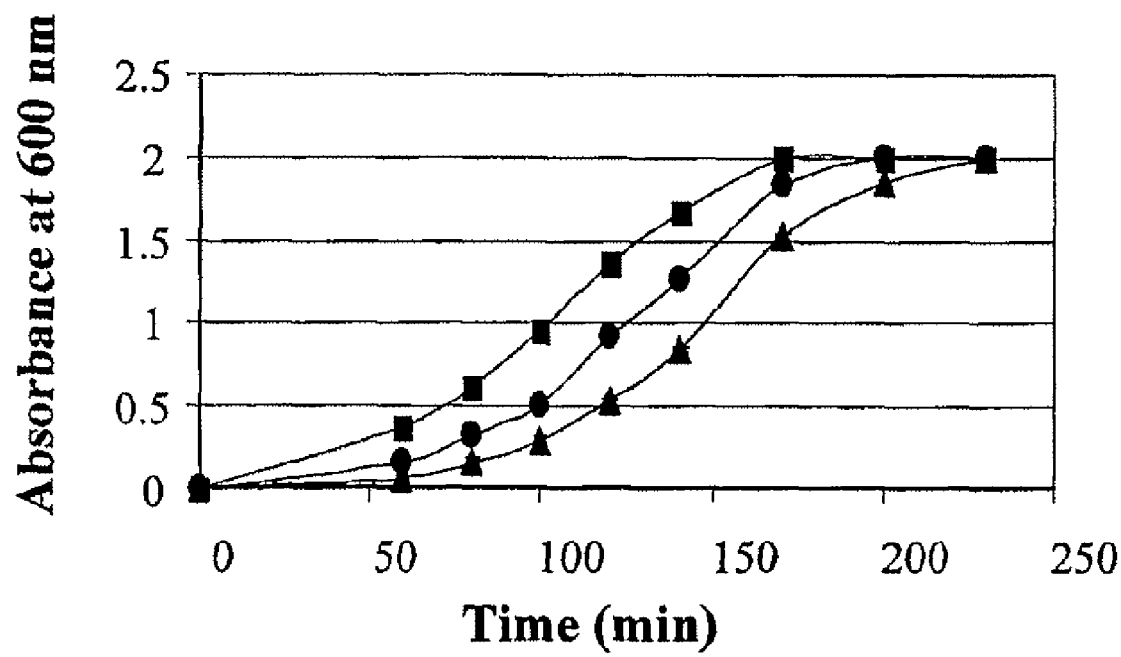
FIG. 11. The effect of drug-carrying peptide-displaying phages on the growth of *Staphylococcus aureus*. (A) Growth curves of SA cells treated with SA-specific chloramphenicol prodrug-conjugated phage A12C (triangles), chloramphenicol prodrug-conjugated irrelevant phage F2b (circles), non conjugated SA-specific phage A12C as negative control (squares). (B) Growth curves of SA cells treated with SA-specific chloramphenicol prodrug-conjugated phage A12C (triangles) or various concentration of free chloramphenicol: 0.533 µg/ml (large filled circles), 1.0625 µg/ml (small open circles), 2.125 µg/ml (large open circles) or cells grown without any growth inhibitor (filled squares). Error bars represent the standard deviation of the data.
Figure 11B:
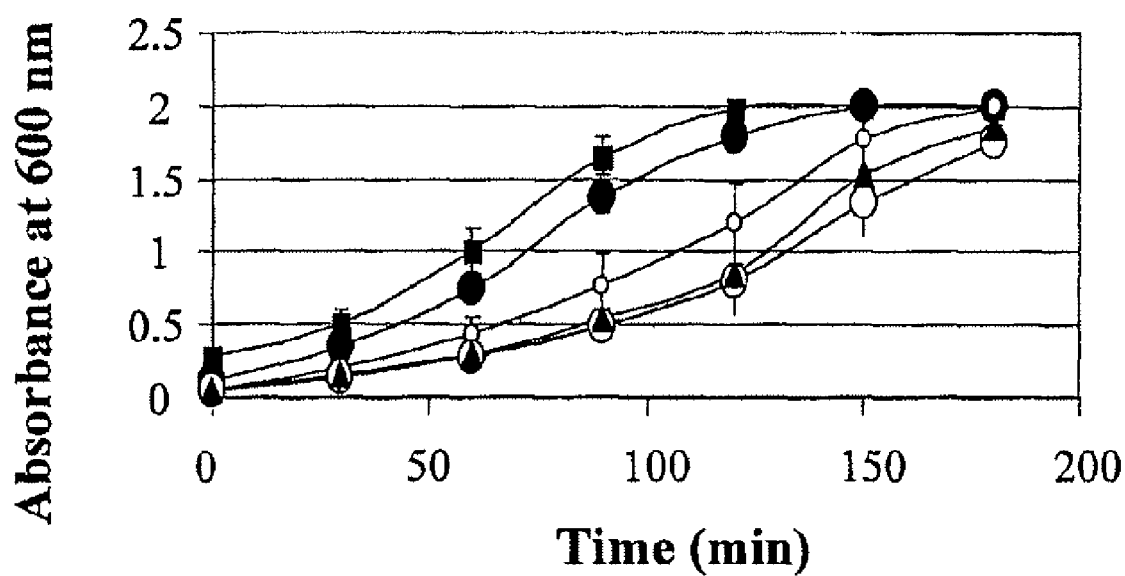

As shown in FIG. 11A, the growth of the SA bacteria was retarded following treatment with the chloramphenicol-conjugated SA-targeted phages in comparison to SA treated with targeted phages that do not carry drug. The control phages that display an irrelevant peptide also retarded the bacterial growth, but to a lesser extent. The equivalent concentration of free chloramphenicol did not retard the bacterial growth. In FIG. 11B, is shown a comparison of growth curves obtained in the presence of varying concentrations of free chloramphenicol to growth in the presence of targeted drug-carrying A12C phages. Under these experimental conditions, the targeted A12C phages release the equivalent of 0.96 µg/ml chloramphenicol. As shown, the phages retarded SA growth as efficiently as ×20 higher concentration of free chloramphenicol.

When fUSE5-ZZ was evaluated, all the binding/targeting studies with *S. aureus* were done following blocking of the bacteria own cell-surface protein A with 20% rabbit serum prior to addition of the specific antibodies. Phage fUSE5-ZZ was conjugated to the chloramphenicol prodrug as described and evaluated for targeted drug delivery as follows: an overnight bacterial culture was diluted ×100 in PBS. 1 ml of diluted bacteria was incubated with human polyclonal anti SA IgG for 1 hr at RT. Next, the cells were collected by centrifugation and re-suspended in 100 µl PBS. 10 µl of this bacterial stock was mixed with $10^{12}$ CFU of fUSE5-ZZ phages in 1 ml of PBS, and then further incubated for 1 h. The tested phages were as follow: 1. chloramphenicol conjugated fUSE5-ZZ phages 2. chloramphenicol-conjugated fUSE5-ZZ phages that were blocked by incubation with normal (non immune) Human IgG (Jackson ImmunoResearch Laboratories, USA), as negative control. 3. fUSE5-ZZ phages without drug as an additional negative control. Cells were incubated with the phages for 1 h followed by incubation with 50% rabbit serum for 1 hr, after which they were diluted directly into 2 ml of TSB medium 20% rabbit serum in 13 ml tubes shaking at 250 RPM at 37° C. Growth was recorded after dilution into the TSB medium by recording the optical density (OD) at 600 nm.

Figure 12:
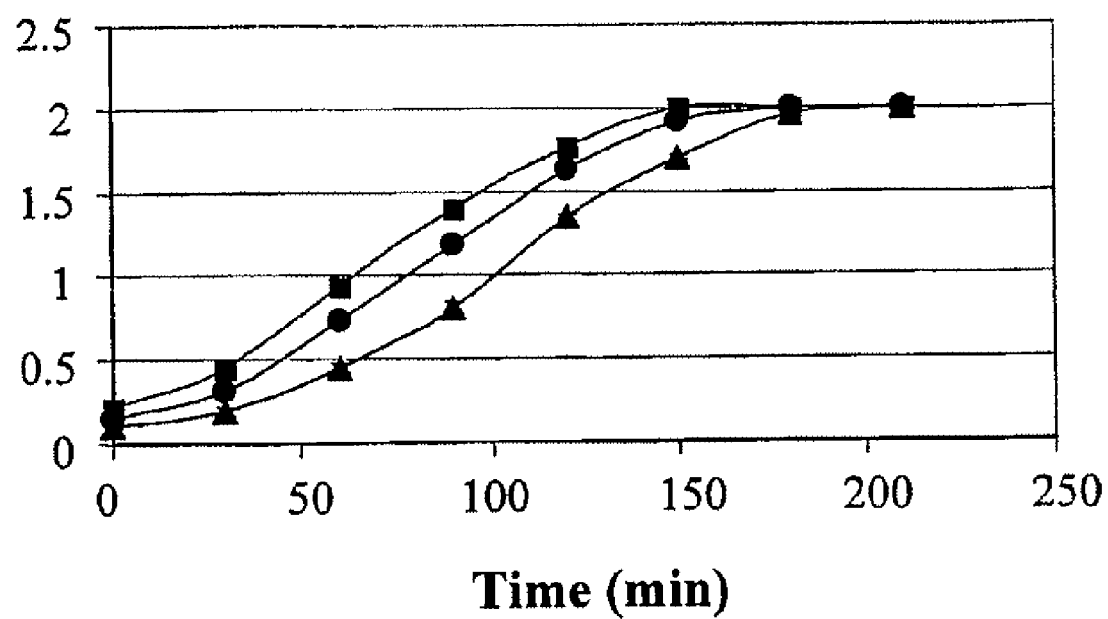
FIG. 12. The effect of drug-carrying, antibody-targeted ZZ-displaying phages on the growth of *Staphylococcus aureus*. Growth curves of SA cells treated with chloramphenicol prodrug-conjugated phage fUSE5-ZZ targeted by anti SA antibodies (triangles), chloramphenicol prodrug-conjugated phage fUSE5-ZZ blocked by control IgG (circles), or cells grown without any growth inhibitor (squares). Error bars represent the standard deviation of the data.

As shown (FIG. 12), chloramphenicol-carrying fUSE5-ZZ phages retarded the growth of the target SA bacteria after they were incubated with SA-specific human antiserum (bound through the displayed ZZ domain) and to a lesser extent when the phages were complexed with a non-immune human IgG that doesn't bind the blocked SA bacteria. In these experiments, targeted fUSE5-ZZ retarded SA growth as effectively as ×10 higher concentration of free chloramphenicol.

Example 8

Aminoglycosides as Drug Solubilization and Bridging Moieties

A. Two Alternative Synthesis Routes were Applied for Conjugation Via an Aminoglycoside Bridge:

For conjugating a hydrophobic cargo, the drug, activated for amine conjugation (in the following experiments, NHS and isothiocynate chemistries were used) was initially reacted in an aqueous solution (NaHCO$_3$ 0.1 M pH=8.5) of an aminoglycoside at a concentration lower than the number of available amine groups (to leave one amine available for the subsequent conjugation to the carrier). The reaction was stirred gently for overnight at room temperature. Then the solution was titrated with HCl and Na-citrate buffer was added to final concentration of 0.1 M (pH=5.5). This solution was brought to a final molar concentration of 0.75 M NaCl and finally the carrier bacteriophages was added followed by immediate addition of EDC at concentration of ×100 molar excess over the target carboxyl side chains of the targeted drug carrier. This reaction was stirred gently for 1-2 hours at room temperature, followed by exhaustive dialysis against PBS/0.3 M NaCl. This process is illustrated in FIG. 13.

For conjugating a hydrophilic drug or a drug with moderate solubility in aqueous buffers, the aminoglycoside moiety was conjugated first to the targeted phages and then the carrier-aminoglycoside complex was reacted with the excess amount of drug that was activated for amine conjugation. Briefly: The solution was titrated with HCl and Na-citrate buffer is added to a final concentration of 0.1 M (pH=5.5). To this solution, a solution of 5M NaCl was added to a final molar concentration 0.75 M and finally the carrier protein was added followed by immediate addition of EDC at concentration of ×100 molar excess of the carboxyl side chains of the carrier. This reaction was stirred gently for 1-2 hours at room temperature, followed by overnight dialysis against a solution of NaHCO$_3$ 0.1 M pH=8.5, which was followed by same dialysis procedure for 3 hours. Next, the carrier-aminoglycoside molecules complex was reacted toward an amine conjugation activated drug. Drug concentration is ×100 molar excess over the carrier amine side chains available for conjugation.

B. Conjugation of FITC to Phage fUSE5-ZZ Through a Hygromycin Bridge.

EDC mediated conjugation of aminoglycosides was first accomplished by using hygromycin as a model linker. hygromycin contains only two primary amines, one for drug conjugation and the other for conjugation to a carrier. Hygromycin was initially conjugated to FITC as described above. Briefly, a molar ratio of 10 hygromycin molecules:1 FITC molecule led to a 10% labeling efficiency and immediate solubilization of FITC. This is an important observation, since the addition of FITC stock solution (38.9 mg/ml in DMSO) to an equal volume of buffer without aminoglycosides results in immediate formation of precipitate.

The product of the FITC-hygromycin conjugate was then divided to two tubes; both were mixed with 1×10$^{12}$ fUSE5-ZZ phage particles. EDC was added to the first tube while the second was used as negative control ("background"). The reaction was mixed for one hour as described above and then dialyzed extensively against PBS. The resulted product was read by fluorometer (excitation wavelength 488 nm and emission filter 533 nm) and the amount of conjugated drug was calculated using calibration curve free FITC. A number of ~10,000 hygromycin molecules/phage was calculated. This number is about the potential carrying capacity of carboxyl attachment since from total amount of 5 carboxyl residues within major coat protein only 3 located to the N-terminus see model structure FIG. 14. The direct conjugation of FITC to phages using identical condition except for the aminoglycoside bridge yielded ~800 Fluorescein molecules linked to the phage coat amine groups. Thus, although hygromycin can not be considered "a branched linker" because it has only two modifiable amines, it provided for improved water solubility of the otherwise poorly soluble FITC on one hand, and for increased carrying potential of the phages because of the exploitation of the carboxyl groups on the phage coat protein for conjugation on the other.

C. Conjugation of Chloramphenicol to Phage fUSE5-ZZ ZZ Through a Kanamycin Bridge.

As describe above, two conjugation methods were applied: in the first, the drug was initially conjugated to aminoglycoside and then the complex was conjugated to the carrier by EDC chemistry. In the second, the aminoglycoside was initially conjugated to carboxyl side chains of the carrier, multiplying amine side chains available for drug conjugation.

Both methods were applied to conjugate chloramphenicol to fUSE5-ZZ phages essentially as described above. The aminoglycoside kanamycin that was chosen as a solubilizing branched linker contains 4 primary amines, 3 may be used for drug conjugation and the fourth for conjugation to the carrier. The antibiotic drug chloramphenicol was activated to amine conjugation by ester conjugation to a linker ended by NHS ester, and then conjugated to kanamycin using both methods. Quantification of total conjugated chloramphenicol was done by serum esterases-mediated release of free chloramphenicol. Briefly, the conjugated phages were mixed at 1:1 v:v ratio with horse serum and incubated for 40 hours at 37° C. The resulted product was then ultra-filtered. The filtrate was read by spectrophotometer at 280 nm and free drug was calculated by a calibration curve of optical density as a function of free chloramphenicol concentration.

An amount of ~35,000 chloramphenicol molecules per phage particle was measured. In comparison, a direct chloramphenicol conjugation without the assistance of the aminoglycoside (as described in Example 4) led to a lower number of a ~5000 chloramphenicol molecules per phage particle. Both conjugation methods yielded a similar number of conjugated drug molecules/phage. In addition, no loss of phage was recorded during the conjugation process.

Example 9

Phage Toxicity

In previous publications, phage preparations were reported to be contaminated with toxic substances originating from lysed bacterial hosts. Our preparations of unmodified and drug-carrying phages were tested for toxicity by IV injection of $10^{12}$ plaque-forming units (PFU) in PBS of 8 weeks-old female Balb/C mice. The mice tolerated the injected phages with no signs of illness or weight loss in comparison to PBS injected control mice.

Example 10

Phage Immunogenicity

In previous reports, peptide-displaying phages were used to immunize female Balb/C mice with the objective of obtaining anti-peptide immunity. Mice were immunized IV or IP, 3 times with $10^{11}$ PFU phages in PBS per injection at 14-day intervals. Seven days after the third injection, mice were bled and their sera examined by ELISA for peptide and anti phage antibody titer. In all these experiments, the anti phage titer after the third injection exceeded $10^5$ (Haus-Cohen et al., 2004).

Herein, fD phages were modified by NHS conjugation and examined by ELISA essay. The results demonstrated that following NHS conjugation, fD phages were no longer recognized by a commercial anti f) phage antibody (Pharmacia) that bind to p8.

Targeted drug-conjugated phages (Examples 5 and 6), or native phages as a control, are used to immunize Balb/C mice as described above. Mice sera are examined by ELISA for anti phage antibody titer using standard procedure.

Example 11

Evaluation of Targeted Drug-Carrying Bacteriophages In Vivo

The targeted drug-carrying bacteriophages of the invention are examined in several in vivo model systems of bacterial infection and tumors.

The Gram-positive pathogenic bacterium *Staphylococcus aureus* has the ability to cause a wide variety of human diseases ranging from superficial abscesses and wound infections to deep and systemic infections, such as osteomyelitis, endocarditis, and septicemia *S. aureus* is a major cause for nocosomial infections and acquires drug resistance at an alarming pace. Peptide and scFv-displaying phages that recognize *S. aureus* are isolated, and protein-A purified anti-*S. aureus* polyclonal rabbit serum is used with the ZZ domain-displaying phages described above. These phages are conjugated to chloramphenicol as described above and tested in two mouse models: a systemic infection model (Mazmanian et al., 2000) where delaying or preventing bacterial colonization of the kidneys or bacteria-induced death as an endpoint, and a superficial skin abscess model (Horsburgh et al., 2002) where limiting the size of the lesion and the number of colonizing *S. aureus* is the endpoint.

The systemic infection experiments are performed as follows: Staphylococci are grown overnight in tryptic soy broth (TSB), diluted into fresh medium, grown for 3 h at 37° C. to OD600 0.5, and washed and diluted in PBS. Six- to eight-week-old C57BLy6 mice or Swiss-Webster mice are inoculated with 500 ml of Staphylococcal suspension into the tail vein. $10^{12}$ CAM-conjugated phages as described in Examples 6 and 7, and serial x10 dilutions thereof, are administered IV, once every two days. Five days after infection, mice are euthanized with $CO_2$, Kidneys are excised, weighed, and homogenized in 0.5% Triton X-100. Staphylococci are counted by dilution and colony formation. All experiments used staphylococcal strains that are subjected to animal passage and isolated from the kidneys of infected mice.

The skin abscess experiments are performed as follows: *S. aureus* strains are grown to the stationary phase in BHI medium (15 h) and then harvested by centrifugation and washed twice in phosphate-buffered saline (PBS). The cell concentrations are adjusted to $5\times10^8$ CFU $ml^{-1}$, and then 200 µl portions of a cell suspension are injected subcutaneously into female 6 to 8-week-old BALB/c mice. An ointment comprising $10^{12}$ drug conjugated phages as described above is placed onto the lesion. After 7 days the mice are euthanized with $CO_2$, and skin lesions are aseptically removed and stored frozen in liquid nitrogen. The lesions are weighed, chopped, and homogenized in a mini-blender in 2.5 ml of ice-cold PBS. After 1 h of incubation on ice, the lesions are homogenized again before serial dilution of the suspension, and the total number of bacteria is counted by growth on BHI agar.

The tumor-associated antigen MUC1 is a unique membrane-bound mucin antigen containing a cytoplasmic, transmembrane and an extracellular domain. MUC1 has received considerable interest as a tumor associated antigen target for several immunotherapeutic modalities. Recently, the inventors cloned and humanized the potent Muc1-specific mAb H23 in the form of a recombinant scFv (Mazor et al., 2005). H23-expressing phages are produced and linked to the drug hygromycin as described above. These targeted drug-carrying phages are evaluated using cultured Muc1-expressing, transformed cell lines (MDA-MB231 and T47D) and tumor xenografts of the same cell lines in nude mice as described below.

IL2Rα (Tac) overexpression is a hallmark of hematological malignancies and is used as a target molecule for targeted immunotherapy. Anti-Tac IgG (Benhar et al., 2000) are used as targetors with the ZZ domain-displaying phages of the invention. In other experiments, anti-Tac scFv derivatives (Benhar et al., 2000) displaying phages are generated as described above, and peptide-displaying anti-Tac phages are isolated. These phages are conjugated to the drug hygromycin as described above. Tac-expressing ATAC4 cells and tumor xenografts of these cells in nude mice (Reiter et al., 1994; Lev et al., 2002) are used to examine these targeted drug-carrying phages.

These experiments are performed as follows: To establish tumor xenografts, female BALB/c athymic nude mice (6-8 weeks old, ~20 g) 3-5 mice per group are injected sub-cutaneously with $1.5\times10^6$ ATAC-4 cells (for the anti-Tac model) or T47D cells (for the H23 model) suspended in 0.2 ml PBS. By day 4-9 post injection, after tumors of about 30-40 $mm^3$ have formed, mice are treated every other day by i.v. injections of different doses of drug-carrying phages diluted in PBS (starting with $10^{12}$ phages as the maximal dose, 3-5 doses are given). Tumors are measured with a caliper at 3-day intervals, and the tumor volumes are calculated according to the formula: volume=(length)×(width)²×(0.4). Animals are sacrificed when tumors reach 2 cm in diameter or when animals appeared to be in distress.

Pharmacokinetics and biodistribution studies are carried out in mice essentially as described (Yip et al., 1999; Zou et al., 2004) with the exception that tumor-bearing mice are examined as well. This is done as follows: mice are injected in the tail vein with $1.5\times10^{10}$ TU phages, either conjugated or non-conjugated to the drug in a total volume of 150 µl in PBS. The phage are allowed to circulate in the mice for 5, 15, 30, 60 min and 24, 48, and 72 h. The mice are then sacrificed by cervical dislocation. Blood is collected and the mice are perfused with 90 ml of sterile PBS prior to organ and tissue retrieval. The organs and tissue are removed, weighed, and stored at −80° C. A portion of the tissue is formalin fixed. The distribution of the phage in the organs and tissues is determined after chopping the frozen tissue with a razor blade followed by douncing in a 2 ml Kontes dounce homogenizer in 500 µl of Dulbecco's Modified Eagles Medium+protease inhibitor+0.25% BSA (DMPB). The tissues are washed three times with 1 ml DMPB. The final tissue pellet is weighed and 500 µl of DMPB containing 0.25% 3-[(3-cholamidopropyl)-dimethylammonio]-1-propanesulfonate (CHAPS) is added to facilitate phage extraction. The samples are placed on a rotator at 4° C. for 1 h. These mixtures are used to infect *E. coli* cells concurrently with appropriate controls to account for variability in phage infectivity. The amount of infectious phage particles in the blood is determined by incubating 50 µl of blood with 500 µl DMPB containing 0.25% CHAPS, rotating at 4° C. for 1 h, prior to infecting the *E. coli*.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

Ausubel, R. M. et al., eds. "Current Protocols in Molecular Biology," Volumes I-III, John Wiley & Sons, Baltimore, Md., 1994.

Babai, R., Blum-Oehler, G., Stem, B. E., Hacker, J. and Ron, E. Z. FEMS Microbiol. Lett. 149, 99-105, 1997.

Bastien, N., Trudel, M. and Simard, C. Virology 234, 118-122, 1997.

Becerril, B., Poul, M. A. and Marks, J. D. Biophys. Res. Commun. 255, 386-93, 1999.

Benhar, I. and Pastan, I. Tumor Targeting by Antibody-Drug Conjugates. In: A. J. Harris W J (Ed) Antibody Therapeutics. CRC Press, Boca Raton, p. 73-85, 1997.

Benhar, I. and Reiter, Y. Phage display of single-chain antibodies. In: J. Colligan (Ed) Current Protocols in Immunology, Vol. 10.19B. John Wiley & Sons, Inc, USA, 2001.

Benhar, I. Biotechnology Advances 19, 1-33, 2001.

Benhar, I., and Y. Reiter. Phage display of single-chain antibodies. In J. C. (Ed), Current Protocols in Immunology. John Wiley & Sons, Inc, USA, 2002.

Benhar, I., R. Azriel, L. Nahary, S. Shaky, Y. Berdichevsky, A. Tamarkin, and W. Wels. J Mol Biol 301, 893-904, 2000.

Berdichevsky, Y., Ben-Zeev, E., Lamed, R. and Benhar, I. J. Immunol. Methods 228, 151-62, 1999.

Borrebaeck, C. A. K. Antibody Engineering (Breakthroughs in Molecular Biology). Oxford University Press, 1995.

Brent, R., Kingston, R. E., Seidman, J. G., Struhl, K., Chanda, V. B., Moore, D. D. and Ausubel, F. M. Current Protocols in Molecular Biology. John Wiley & Sons Inc., 2003.

Brown W L, Mastico R A, Wu M, Heal K G, Adams C J, Murray J B, Simpson J C, Lord J M, Taylor-Robinson A W, Stockley P G. Intervirology, 45(4-6), 371-80, 2002.

Carbonell, X. and Villaverde, A. Gene 176, 225-9, 1996.

Clark, J. R. and March, J. B. FEMS Immunol. Med. Microbiol. 40, 21-26, 2004.

Delmastro, P., Meola, A., Monaci, P., Cortese, R and Galfre, G. Vaccine 15, 1276-1285, 1997.

Efimov, V. P., Nepluev, I. V. and Mesyanzhinov, V. V. Virus Genes 10, 173-7, 1995.

Enshell-Seijffers, D., and J. M. Gershoni. Phage display selection and analysis of Ab-binding epitopes. In J. C. (Ed). (ed.), Current Protocols in Immunology. John Wiley & Sons, Inc, USA, 2002.

Enshell-Seijffers, D., Smelyanski, L. and Gershoni, J. M. Nucleic Acids Res. 29, E50, 2001.

Felnerova D, Viret J F, Gluck R, Moser C. Curr Opin Biotechnol. December; 15(6), 518-29, 2004.

Freeman, A., N. Cohen-Hadar, S. Abramov, R. Modai-Hod, Y. Dror, and G. Georgiou. 2004. Biotechnol Bioeng 86, 196-200, Garcea et al., Curr Opin Biotechnol. 15(6), 513-7, 2004.

Goodman and Gilman, The Pharmacological Basis of Therapeutics, Eighth Edition, McGraw-Hill, Inc. (Health Professions Division), 1990.

Haimovich J, Sela M. Science, June 13; 164(885), 1279-80, 1969.

Haus-Cohen, M., Assaraf, Y. G., Binyamin, L., Benhar, I. and Reiter, Y. Int J Cancer 109, 750-8, 2004.

Heal, K. G., Hill, H. R., Stockley, P. G., Hollingdale, M. R. and Taylor-Robinson, A. W. Vaccine 18, 251-8, 1999.

Held, H. A. and Sidhu, S. S. J. Mol. Biol. 340, 587-97, 2004.

Hong, Y. R. and Black, L. W. Gene 136, 193-8, 1993.

Horsburgh, M. J., Aish, J. L., White, I. J., Shaw, L., Lithgow, J. K. and Foster, S. J. J Bacteriol 184, 5457-5467, 2002.

Kassner, P. D., Burg, M. A., Baird, A. and Larocca, D. Biochem. Biophys. Res. Commun. 264, 921-8, 1999.

Kay, B., Winter, J. and McCafferty, J. Phage Display of Peptides and Proteins: A Laboratory Manual. Academic Press, 1996.

Larocca, D. and Baird, A. Drug Disc. Today 6, 793-801, 2001.

Larocca, D., Jensen-Pergakes, K., Burg, M. A. and Baird, A. Mol. Therap. 3, 2001.

Lee, C. S. and Guo, P. J. Virol. 69, 5018-23, 1995.

Lev, A., Novak, H., Segal, D. and Reiter, Y. J Immunol 169, 2988-96, 2002.

Lo, B. K. C. Antibody Engineering: Methods and Protocols (Methods in Molecular Biology). Humana Press, 2003.

Malik, P., Terry, T. D., Gowda, L. R., Langara, A., Petukhov, S. A., Symmons, M. F., Welsh, L. C., Marvin, D. A. and Perham, R. N. J. Mol. Biol. 260, 9-21, 1996.

Maruyama, I. N., Maruyarna, H. I. and Brenner, S. Proc. Natl. Acad. Sci. (USA) 91, 8273-8277, 1994.

Mazmanian, S. K., Liu, G., Jensen, E. R., Lenoy, E. and Schneewind, O. Proc Natl Acad Sci USA 97, 5510-5515, 2000.

Mazor, Y., Keydar, I. and Benhar, I. Mol. Immunol. 42(1), 55-69, 2005.

Menendez, T., De Haz, I., Delgado, M., Garay, H., Martin, A. and Vispo, N. S. Immunol. Lett. 78, 143-8, 2001.

Meola, A., Delmastro, P., Monaci, P., Luzzago, A., Nicosia, A., Felici, F., Cortese, R. and Galfre, G. J. Immunol. 154, 3162-3172, 1995.

Merril, C. R., Biswas, B., Carlton, R., Jensen, N. C., Creed, G. J., Zullo, S, and Adhya, S. Proc. Natl. Acad. Sci. (USA) 93, 3188-3192, 1996.

Mikawa, Y. G., Maruyama, I. N. and Brenner, S. J. Mol. Biol. 262, 21-30, 1996.

Nakamura, M., Tsumoto, K., Ishimura, K. and Kumagai, I. Biochem. Biophys. Res. Commun. 289, 252-6, 2001.

Nakamura, M., Tsumotob, K., Ishimuraa, K. and Kumagaib, I. FEBS Lett. 520, 77-80, 2002.
Nilsson, B., Moks, T., Jansson, B., Abrahmsen, L., Elmblad, A., Holmgren, E., Henrichson, C., Jones, T. A. and Uhlen, M. Protein Eng. 1, 107-13, 1987.
Phalipon, A., Folgori, A., Arondel, J., Sgaramella, G., Fortugno, P., Cortese, R., Sansonetti, P. J. and Felici, F. Eur. J. Immunol. 27, 2620-2625, 1997.
Physician's Desk Reference, 50th Ed, Medical Economics, 1996.
Poul, M. A. and Marks, J. D. J. Mol. Biol. 288, 203-11, 1999.
Poul, M. A., Becerril, B., Nielsen, U. B., Morisson, P. and Marks, J. D. J. Mol. Biol. 301, 1149-61, 2000.
Reiter, Y., Kreitman, R. J., Brinkmann, U. and Pastan, I. Int J Cancer 58, 142-9, 1994.
Remington's Pharmaceutical Sciences, 15th Ed. Easton: Mack Publishing Co. pp 1405-1412 and 1461-1487, 1975.
Ren, Z. and Black, L. W. Gene 215, 439-44, 1998.
Saggio, I., Gloaguen, I. and Laufer, R. Gene 152, 35-39, 1995.
Sambrook, J., Russell, D. W. and Maniatis, T. Molecular cloning: A laboratory manual. Cold Spring Harbor Laboratory, Cold Spring Harbor, N.Y., 1989.
Sidhu, S. S. Biomolecular Eng. 18, 57-63, 2001.
Smith, G. P. and Scott, J. K. Methods Enzymol 217, 228-57, 1993.
Smith, G. P., Petrenko, V. A. and Matthews, L. J. J. Immunol. Methods 215, 151-61, 1998.
Sternberg, N. and Hoess, R. H. Proc. Natl. Acad. Sci. (USA) 92, 1609-13, 1995.
Sulica A, Haimovich J, Sela M. J. Immunol., March; 106(3), 721-31, 1971.
Summers, W. C. Ann. Rev. Microbiol. 55, 437-51, 2001.
The National Formulary XIV., 14th Ed. Washington: American Pharmaceutical Association, 1975.
Ulbrich, K. and Subr, V. Adv. Drug Delivery Rev. 56, 1023-1050, 2004.
Uppala, A. and Koivunen, E. Comb. Chem. High Throughput Screen. 3, 373-392, 2000.
Urbanelli, L., Ronchini, C., Fontana, L., Menard, S., Orlandi and Monaci, P. J. Mol. Biol. 313, 965-976, 2001.
White, C. A., Weaver, R. L. and Grillo-Lopez, A. J. Annu. Rev. Med. 52, 12545, 2001.
Yip, Y. L., Hawkins, N. J., Smith, G. and Ward, R. L. J Immunol Methods 225,171-8, 1999.
Zou, J., Dickerson, M. T., Owen, N. K., Landon, L. A. and Deutscher, S. L. Mol Biol Rep 31,121-9, 2004.

---

What is claimed is:

1. A pharmaceutical composition comprising a bacteriophage-drug conjugate, wherein an average of at least 3,000 drug molecules is conjugated to an outer surface of each bacteriophage, wherein the bacteriophage is a filamentous bacteriophage genetically modified to display an exogenous targeting moiety that selectively binds a cell surface target molecule on a target cell, and wherein the bacteriophage is covalently linked to the drug via a labile linker which upon cleavage releases the drug, wherein said linker comprises a hydrophilic aminoglycoside having two or more reactive amine residues.

2. The composition of claim 1, wherein the bacteriophage is conjugated to an average of at least 5,000 or at least 10,000 drug molecules.

3. The composition of claim 1, wherein the linker comprises a branched linker or a dendrimer.

4. The composition of claim 1, wherein the bacteriophage is a filamentous bacteriophage selected from the group consisting of m13, Fd and f1.

5. The composition of claim 1, wherein the targeting moiety is selected from the group consisting of an antibody, an antibody fragment, a peptide, a polypeptide, a carbohydrate, a lipid, a glycolipid, and a nucleic acid.

6. The composition of claim 1, wherein the targeting moiety comprises a ligand selected from the group consisting of the ZZ domain derived from *Staphylococcus aureus* protein A, avidin, streptavidin, biotin and derivatives thereof, wherein the ligand is bound to a targeting molecule that selectively binds the target molecule on the target cell, said targeting molecule being selected from the group consisting of an antibody, an antibody fragment, a peptide, a polypeptide, a carbohydrate, a lipid, a glycolipid, and a nucleic acid.

7. The composition of claim 1, wherein the targeting moiety or a component thereof is encoded by a nucleic acid fused to a gene encoding a coat protein of the bacteriophage.

8. The composition of claim 1, wherein the targeting moiety or a component thereof is linked to the phage by means of chemical conjugation.

9. The composition of claim 6, wherein the bacteriophage is a filamentous bacteriophage comprising a coat protein fused to a ligand comprising the ZZ domain derived from *Staphylococcus aureus* protein A.

10. The composition of claim 1, wherein the target cell is selected from the group consisting of a bacterial cell, a fungal cell, a yeast cell, a unicellular parasite cell, a multicellular parasite cell and a mammalian cell.

11. The composition of claim 10, wherein the target molecule on the target cell is selected from the group consisting of MUC-1 and Tac.

12. The composition of claim 1, wherein the drug is selected from the group consisting of: an antibacterial agent, an antibiotic, an antifungal drug, an antiviral drug, a parasiticide, a cytotoxic agent, and a cytostatic agent.

13. The composition of claim 1, wherein the targeting moiety is selected such that the bacteriophage-drug conjugate is not internalized.

14. The composition of claim 1, wherein the drug is a hydrophobic drug.

15. The composition of claim 1, wherein the drug is in the form of an inactive prodrug, which, upon the cleavage of the linker is released in an active drug form.

16. The composition of claim 1, wherein said cleavage is facilitated by an enzymatic activity selected from the group consisting of an enzymatic activity present on the surface of the target cell, an enzymatic activity present inside the target cell, an enzymatic activity present in bodily fluids, an exogenous enzyme administered to a subject and an enzymatic activity facilitated by an enzyme encoded by a nucleic acid delivered to the target cell by the bacteriophage.

17. The composition of claim 1, wherein said cleavage is facilitated by at least one enzyme selected from the group consisting of proteases, peptidases, esterases, amidases, glycosidases and lipases.

18. The composition of claim 1, wherein said cleavage is facilitated by acidic pH.

19. The composition of claim 3, wherein said composition carries a plurality of drugs.

20. The composition of claim 1 further comprising a pharmaceutically acceptable excipient or diluent.

21. A bacteriophage-drug conjugate comprising an average of at least 3,000 drug molecules conjugated to the outer surface of the bacteriophage, with the bacteriophage displaying an exogenous targeting moiety that binds a cell surface molecule on a target cell, wherein said bacteriophage is covalently linked to the drug via a labile linker which upon cleavage releases the drug, and wherein said linker comprises a hydrophilic aminoglycoside having two or more reactive amine residues.

22. A method of treating a disease in a subject in need thereof, comprising administering to the subject a therapeutically effective amount of a pharmaceutical composition according to claim 1.

23. The method of claim 22, wherein the bacteriophage displays an exogenous targeting moiety which binds a cell surface molecule on a target cell.

24. The method of claim 22, wherein the disease is selected from: a bacterial infection, a viral infection, a fungal infection, a yeast infection, a parasitic infection, a non-infectious disease or disorder, an autoimmune disease, a hyperproliferative disorder, restenosis, an angiogenesis-dependent disease and cancer.

25. The method of claim 22, wherein the subject is selected from the group consisting of mammals and non-mammalian animals.

26. The method of claim 25, wherein the subject is human.

27. The method of claim 26, wherein the bacteriophage comprises a nucleic acid molecule comprising an exogenous nucleic acid sequence that is transcribed and translated in the target cell.

28. The method of claim 27, wherein the exogenous nucleic acid sequence encodes a polypeptide or peptide selected from the group consisting of an antimicrobial peptide, an antibiotic, a toxin, an enzyme and a cytotoxic agent.

29. The method of claim 28, wherein the exogenous nucleic acid sequence encodes an enzyme which is capable of cleaving the linker connecting the drug to the bacteriophage, thereby releasing the drug.

30. A method of treating a bacterial infestation, comprising exposing the bacteria to a bacteriophage-drug conjugate according to claim 21.

31. The method of claim 30, wherein the bacteriophage is capable of lysing the bacteria.

32. A kit for generating a targeted bacteriophage-drug conjugate, comprising:
(i) a bacteriophage-drug conjugate displaying a ligand capable of binding a targeting molecule that selectively binds a target molecule on a target cell, wherein an average of at least 3,000 drug molecules are conjugated to the outer surface of the bacteriophage, wherein said bacteriophage is covalently linked to the drug via a labile linker which upon cleavage releases the drug, and wherein said linker comprises a hydrophilic aminoglycoside having two or more reactive amine residues; and
(ii) instructions for linking the targeting molecule to the ligand.

33. The kit of claim 32, wherein the ligand is selected from the group consisting of the ZZ domain derived from *Staphylococcus aureus* protein A, avidin, streptavidin, and biotin.

34. The composition of claim 9, wherein the coat protein has an amino acid sequence as set forth in SEQ ID NO: 1.

35. The composition of claim 34, wherein said coat protein is encoded by a nucleotide sequence having a nucleic acid sequence as set forth in SEQ ID NO:2.

36. A pharmaceutical composition comprising a bacteriophage-drug conjugate, wherein the bacteriophage is covalently linked to the drug via a hydrophilic aminoglycoside linker having two or more reactive amine residues, bonded to the bacteriophage and/or the drug by a labile bond.

37. The composition of claim 36, wherein the aminoglycoside linker is bonded to the drug by a labile bond.

38. The composition of claim 36, wherein the aminoglycoside linker is bonded to the bacteriophage by a labile bond and is bonded to the drug by a labile bond.

39. The composition of claim 36, wherein the drug is a hydrophobic drug.

* * * * *